(12) United States Patent
Lee

(10) Patent No.: US 6,219,584 B1
(45) Date of Patent: Apr. 17, 2001

(54) METHOD AND SYSTEM FOR DETERMINING AN EFFECTIVE AMOUNT OF LIGHT ENERGY TO DELIVERY TO FLUIDS HAVING TARGETS FOR THE LIGHT ENERGY

(75) Inventor: Kyu Ho Lee, Bryn Mawr, PA (US)

(73) Assignee: Therakos, Inc., Exton, PA (US)

( * ) Notice: Subject to any disclaimer, the term of this patent is extended or adjusted under 35 U.S.C. 154(b) by 0 days.

(21) Appl. No.: 09/350,134

(22) Filed: Jul. 9, 1999

(51) Int. Cl.⁷ .................................................. G06F 17/00

(52) U.S. Cl. ............................... 700/90; 604/4; 604/20; 604/28; 606/7; 606/15; 606/322; 600/6.08; 607/92; 436/519-523; 700/79; 700/80; 700/83; 700/84

(58) Field of Search .................................. 700/90, 79, 80, 700/83, 84; 600/6.08; 604/4, 20, 28; 422/44, 22, 24; 128/898; 607/92; 436/519-523; 606/7, 15, 322

(56) References Cited

U.S. PATENT DOCUMENTS

| | | | |
|---|---|---|---|
| D. 298,279 | 10/1988 | Lee et al. .............................. D24/51 |
| D. 298,567 | 11/1988 | Morris .................................. D24/51 |
| D. 299,531 | 1/1989 | Troutner et al. ..................... D24/1.1 |
| D. 299,953 | 2/1989 | King et al. ........................... D24/1.1 |
| 4,196,281 | 4/1980 | Hearst et al. .......................... 536/28 |
| 4,260,630 | * 4/1981 | Bisagni et al. ...................... 424/283 |
| 4,321,919 | 3/1982 | Edelson ................................ 128/214 |
| 4,398,906 | 8/1983 | Edelson .................................. 604/6 |
| 4,428,744 | 1/1984 | Edelson .................................. 604/6 |
| 4,452,811 | 6/1984 | della Valle .......................... 424/281 |
| 4,464,166 | 8/1984 | Edelson .................................. 604/6 |
| 4,464,354 | 8/1984 | Bisagni et al. ........................ 424/59 |
| 4,465,691 | 8/1984 | Bisagni et al. ...................... 424/256 |
| 4,568,328 | 2/1986 | King ...................................... 604/6 |
| 4,573,960 | 3/1986 | Goss ...................................... 604/6 |
| 4,573,961 | 3/1986 | King ...................................... 604/6 |
| 4,573,962 | 3/1986 | Troutner ................................ 604/6 |
| 4,578,056 | 3/1986 | King et al. ............................ 604/6 |
| 4,596,547 | 6/1986 | Troutner ................................ 604/4 |
| 4,612,007 | 9/1986 | Edelson ................................ 604/5 |
| 4,613,322 | 9/1986 | Edelson ................................ 604/6 |
| 4,623,328 | 11/1986 | Hartranft .............................. 604/4 |
| 4,643,710 | 2/1987 | Troutner .............................. 494/60 |
| 4,681,568 | 7/1987 | Troutner ............................ 604/250 |
| 4,683,889 | 8/1987 | Edelson .............................. 128/395 |
| 4,684,521 | 8/1987 | Edelson .............................. 424/101 |
| 4,687,464 | 8/1987 | Troutner ................................ 604/4 |
| 4,692,138 | 9/1987 | Troutner et al. ...................... 604/4 |

(List continued on next page.)

FOREIGN PATENT DOCUMENTS

| | | |
|---|---|---|
| 0 284 409 A2 | 9/1988 | (EP) . |
| WO 93/14791 | 8/1993 | (WO) . |
| WO 95/03814 | 2/1995 | (WO) . |

OTHER PUBLICATIONS

Yang et al., "The Bllod Cell Counting and Classification fraom Stationary Suspensions by Laser Light Scattering Method", IEEE., pp. 1855–1888, 1998.*

Diehl et al., "Optimisation of a Blood Separation Process Based on Simulation", IEEE., pp. 19–26, 1998.*

Mitzan et al., "Spontaneous Fluctuation in the Tissue Blood Volume and the Systolic Blood Volume Increase", IEEE., pp. 228–230, 1996.*

(List continued on next page.)

Primary Examiner—William Grant
Assistant Examiner—McDieunel Marc
(74) Attorney, Agent, or Firm—McKenna & Cuneo, LLP

(57) ABSTRACT

Systems and methods for determining an effective amount of light energy to deliver to fluids, particularly fluids having target and non-target materials. The systems and methods specifically relate to phototherapy and photopheresis systems where an effective amount of light energy is desired to be delivered to targets in biological fluids.

159 Claims, 13 Drawing Sheets

U.S. PATENT DOCUMENTS

| | | | |
|---|---|---|---|
| 4,693,981 | 9/1987 | Wiesehahn et al. | 435/238 |
| 4,705,498 | 11/1987 | Goss | 604/6 |
| 4,708,715 | 11/1987 | Troutner et al. | 604/6 |
| 4,726,949 | 2/1988 | Miripol et al. | 424/101 |
| 4,727,027 | 2/1988 | Wiesehahn et al. | 435/173 |
| 4,737,140 | 4/1988 | Lee et al. | 604/4 |
| 4,748,120 | 5/1988 | Wiesehahn | 435/173 |
| 4,838,852 | 6/1989 | Edelson et al. | 604/4 |
| 4,866,282 | 9/1989 | Miripol et al. | 250/455.1 |
| 4,897,789 | 1/1990 | King et al. | 604/6.08 |
| 4,921,473 | 5/1990 | Lee et al. | 494/27 |
| 4,952,812 | 8/1990 | Miripol et al. | 250/455.1 |
| 4,960,408 | 10/1990 | Klainer et al. | 604/4 |
| 4,999,375 | 3/1991 | Bachynsky et al. | 514/455 |
| 5,030,200 | 7/1991 | Judy et al. | 604/5 |
| 5,176,921 | 1/1993 | Wiesehahn et al. | 424/529 |
| 5,216,176 | 6/1993 | Heindel et al. | 549/280 |
| 5,288,605 | 2/1994 | Lin et al. | 435/902 |
| 5,356,929 | 10/1994 | Heindel et al. | 514/455 |
| 5,360,734 | 11/1994 | Chapman et al. | 435/238 |
| 5,459,030 | 10/1995 | Lin et al. | 435/2 |
| 5,482,828 | 1/1996 | Lin et al. | 435/2 |
| 5,522,868 * | 6/1996 | Buckley et al. | 607/94 |
| 5,618,662 * | 4/1997 | Lin et al. | 435/2 |
| 5,651,993 | 7/1997 | Edelson et al. | 424/534 |
| 5,820,872 * | 10/1998 | Edelson et al. | 424/277.1 |
| 5,845,255 * | 12/1998 | Mayaud | 705/3 |
| 5,922,278 * | 7/1999 | Chapman et al. | 422/22 |
| 5,925,034 * | 7/1999 | Buckley et al. | 606/7 |

OTHER PUBLICATIONS

Bolz et al., "First Results on an Implantable Sensor for Blood Flow Measurement", IEEE., pp. 2341–2343, 1997.*

Lee et al., "Engineering Aspects of Extracorporeal Photochemotherapy", *The Yale Journal of Biology and Medicine*, dated Jun. 9, 1989, pp. 621–628.

Therakos, Inc., "The UVAR XTS System: Engineering That Reflects Innovation", dated Mar. 1998.

Edelson et al., "Treatment of Cutaneous T–Cell Lymphoma by Extracorporeal Photochemotherapy", *New England Journal of Medicine*, vol. 316, No. 6, dated Feb. 5, 1987, pp. 297–303.

Margolis–Nunno et al., "Elimination of Potential Mutagenicity in Platelet Concentrates that are Virally Inactivated with Psoralens and Ultraviolet A Light", *Transfusion*, vol. 35, No. 10, dated 1995, pp. 855–862.

Hoofnagle et al., "Treatment of Chronic Non–A, Non–B Hepatitis with Recombinant Human Alpha Interferon", *The New England Journal of Medicine*, vol. 315, No. 25, dated Dec. 18, 1986, pp. 1575–1578.

Davis et al., "Treatment of Chronic Hepatitis C with Recombinant Interferon Alfa", *The New England Journal of Medicine*, vol. 321, No. 22, dated Nov. 30, 1989, pp. 1501–1505.

Di Bisceglie et al., "Recombinant Interferon Alfa Therapy for Chronic Hepatitis C", *The New England Journal of Medicine*, vol. 321, No. 22, dated Nov. 30, 1989, pp. 1506–1510.

Farci et al., "A Long–Term Study of Hepatitis C Virus Replication in Non–A, Non–B Hepatitis", *The New England Journal of Medicine*, vol. 325, No. 2, dated Jul. 11, 1991, pp. 98–104.

Shindo et al., "Decrease in Serum Hepatitis C Viral RNA During Alpha–Interferon Therapy for Chronic Hepatitis C", *Annals of Internal Medicine*, vol. 115, No. 9, dated Nov. 1, 1991, pp. 700–704.

Gomez–Rubio et al., "Prolonged Treatment (18 months) of Chronic Hepatitis C with Recombinant α–Interferon in Comparison with a Control Group", *Journal of Hepatology*, vol. 11, dated 1990, pp. S63–S67.

Saez–Royuela et al., "High Doses of Recombinant α–Interferon or γ–Interferon for Chronic Hepatitis C: A Randomized, Controlled Trial", *Hepatology*, vol. 13, No. 2, dated 1991, pp. 327–331.

Nakano et al., "Comparative Study of Clinical, Histological, and Immunological Responses to Interferon Therapy in Type Non–A, Non–B, and Type B Chronic Hepatitis", *The American Journal of Gastroenterology*, vol. 85, No. 1, dated Jan. 1990, pp. 24–29.

Hayashi et al., "Improvement of Serum Aminotransferase Levels After Phlebotomy in Patients with Chronic Active Hepatitis C and Excess Hepatic Iron", *The American Journal of Gastroenterology*, vol. 89, No. 7, dated Jul. 1994, pp. 986–988.

Ljunggren et al., "Plasma Levels of 8–Methoxypsoralen Determined by High–Pressure Liquid Chromatography in Psoriatic Patients Ingesting Drug from Two Manufacturers", *The Journal of Investigative Dermatology*, vol. 74, No. 1, dated Jan. 1980, pp. 59–62.

Jansen et al., "Inter– and Intraindividual Variations in Serum Methoxsalen Levels During Repeated Exposure", *Current Therapeutic Research*, vol. 33, No. 2, dated Feb. 1983, pp. 258–264.

Clemens et al., "Regulation of Cell Proliferation and Differentiation by Interferons", *Biochem*, vol. 226, dated 1985, pp. 345–360.

Witter et al., "Effects of Prednisone, Aspirin, and Acetaminophen on an In Vivo Biologic Response to Interferon in Humans", *Clin. Pharmacol. Ther.*, vol. 44, No. 2, dated Aug. 1988, pp. 239–243.

Rook et al., "Combined Therapy for Sezary Syndrome with Extracorporeal Photochemotherapy and Low–Dose Interferon Alfa Therapy", dated Oct. 1991, pp. 1535–1540.

Rook et al., "Treatment of Autoimmune Disease with Extracorporeal Photochemotherapy: Pemphigus Vulgaris—Preliminary Report", *The Yale Journal of Biology and Medicine*, vol. 62, dated 1989, pp. 647–652.

Barr et al., "Immunomodulation with Photopheresis: Clinical Results of the Multi–Center Cardiac Transplantation Study", one page.

Costanzo–Nordin et al., "Successful Treatment of Heart Transplant Rejection with Photopheresis", *Transplantation*, vol. 53, No. 4, dated Apr. 1992, pp. 808–815.

Meiser et al., "Reduction of the Incidence of Rejection by Adjunct Immunosuppression With Photochemotherapy After Heart Transplantation", *Transplantation*, vol. 57, No. 4, dated Feb. 1994, pp. 563–568.

Vowels et al., "Extracorporeal Photochemotherapy Induces the Production of Tumor Necrosis Factor–α by Monocytes: Implications for the Treatment of Cutaneous T–Cell Lymphoma and Systemic Sclerosis", *The Journal of Investigative Dermatology*, dated May 1992, pp. 686–692.

Campbell et al., "HCV RNA Peripheral Blood Mononuclear Cells of Chronic Hepatitis C Patients Treated with Interferon Alfa–2b: Another Possible Indicator of Response?", one page.

Gil et al., "Hepatic and Extrahepatic HCV RNA Strands in Chronic Hepatitis C: Different Patterns of Response to Interferon Treatment", *Hepatology*, vol. 18, No. 5, dated Nov. 1993, pp. 1050–1054.

Qian et al., "Replication of Hepatitis C Virus in Peripheral Blood Mononuclear Cells", *Journal of Hepatology,* vol. 16, dated 1992, pp. 380–383.

Mendoza et al., "Decreased Phorbol Myristate Acetate—Induced Release of Tumor Necrosis Factor–α and Interleukin–1β from Peripheral Blood Monocytes of Patients Chronically Infected with Hepatitis C Virus", *The Journal of Infectious Diseases,* vol. 174, dated Oct. 1996, pp. 842–844.

Zignego et al., "Infection of Peripheral Mononuclear Blood Cells by Hepatitis C Virus", *Journal of Hepatology,* vol. 15, dated 1992, pp. 382–386.

Shirai et al., "Induction of Cytotoxic T Cells to a Cross–Reactive Epitope in the Hepatitis C Virus Nonstructural RNA Polymerase–Like Protein", *Journal of Virology,* dated Jul. 1992, pp. 4098–4106.

Kanai et al., "Suppression of Hepatitis C Virus RNA by Interferon–α", *The Lancet,* vol. 336, p. 245.

Weiner et al., "Evidence for Immune Selection of Hepatitis C Virus (HCV) Putative Envelope Glycoprotein Variants: Potential Role in Chronic HCV Infections", *Proc. Natl. Acad. Sci., USA,* vol. 89, dated Apr. 1992, pp. 3468–3472.

Garson et al., "Enhanced Detection by PCR of Hepatitis C Virus RNA", *The Lancet,* vol. 336, dated Oct. 6, 1990, pp. 878–879.

Shimizu et al., "Early Events in Hepatitis C Virus Infection of Chimpanzees", *Proc. Natl. Acad. Sci., USA,* vol. 87, dated Aug. 1990, pp. 6441–6444.

Simmonds et al., "Classification of Hepatitis C Virus Into Six Major Genotypes and a Series of Subtypes by Phylogenetic Analysis of the NS–5 Region", *The Journal of General Virology,* vol. 74, dated 1993, pp. 2391–2399.

Houghton et al., "Molecular Biology of the Hepatitis C Viruses: Implications for Diagnosis, Development and Control of Viral Disease", *Hepatology,* vol. 14, No. 2, dated 1991, pp. 381–388.

Choo et al., "Genetic Organization and Diversity of the Hepatitis C Virus", *Proc. Natl. Acad. Sci. USA,* vol. 88, dated Mar. 1991, pp. 2451–2455.

Koretz et al., "Non–A, Non–B Posttransfusion Hepatitis—A Decade Later", *Gastroenterology,* vol. 88, No. 5, dated May 1985, pp. 1251–1254.

Jules L. Dienstag, "Non–A, Non–B Hepatitis. I. Recognition, Epidemiology, and Clinical Features", *Gastroenterology,* vol. 85, No. 2, dated 1983, pp. 439–462.

Choo et al., "Isolation of a cDNA Clone Derived from a Blood–Borne Non–A, Non–B Viral Hepatitis Genome", *Science,* vol. 244, dated Apr. 21, 1989, pp. 359–362.

*Progress,* vol. 16, dated 1994–1995, pp. 1–12.

Watson et al., "High–Dose Interferon Alfa–2A for the Treatment of Chronic Hepatitis C", *The Annals of Pharmacotherapy,* vol. 28, dated Mar. 1994, pp. 341–342.

Rossetti et al., "Extracorporeal Photochemotherapy as Single Therapy for Extensive, Cutaneous, Chronic Graft–Versus–Host Disease", *Transplantation,* vol. 59, No. 1, dated Jan. 15, 1995, pp. 149–151.

Rook et al., "Treatment of Systemic Sclerosis With Extracorporeal Photochemotherapy", *Arch Dermatol,* vol. 128, dated Mar. 1992, pp. 337–346.

Malawista et al ., "Treatment of Rheumatoid Arthritis by Extracorporeal Photochemotherapy", *Arthritis and Rheumatism,* vol. 34, No. 6, dated Jun. 1991, pp. 646–654.

Edelson et al., "Treatment of Cutaneous T–Cell Lymphoma by Extracorporeal Photochemotherapy", *New England Journal of Medicine,* vol. 316, dated Feb. 5, 1987, pp. 297–304.

Richard L. Edelson, "Photopheresis: A Clinically Relevant Immunobiologic Response Modifier", *Annals of New York Academy of Sciences,* pp. 154–164.

Grass et al., "Inactivation of Leukocytes in Platelet Concentrates by Photochemical Treatment With Psoralen Plus UVA", *Blood,* vol. 91, No. 6, dated Mar. 15, 1998, pp. 2180–2188.

* cited by examiner

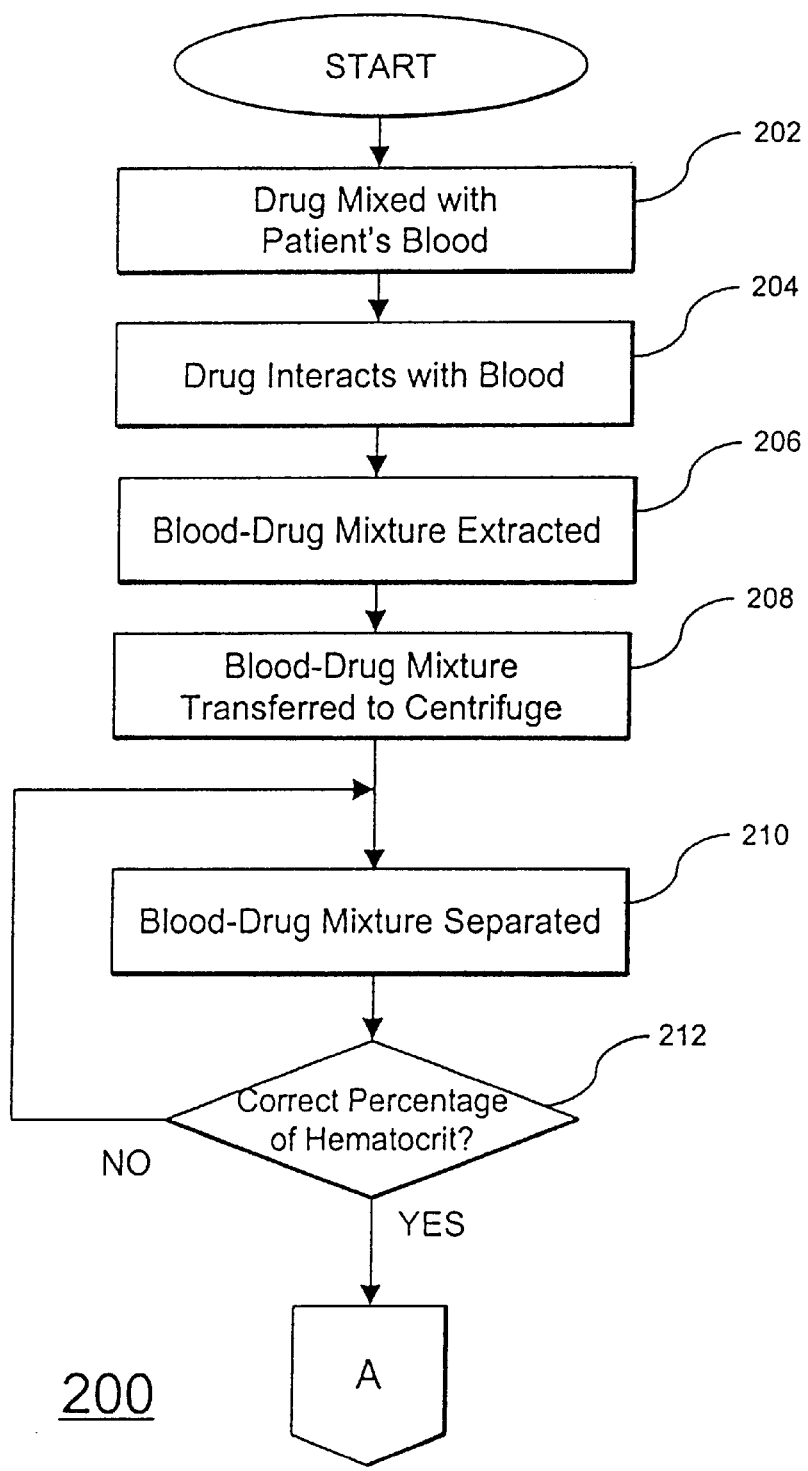

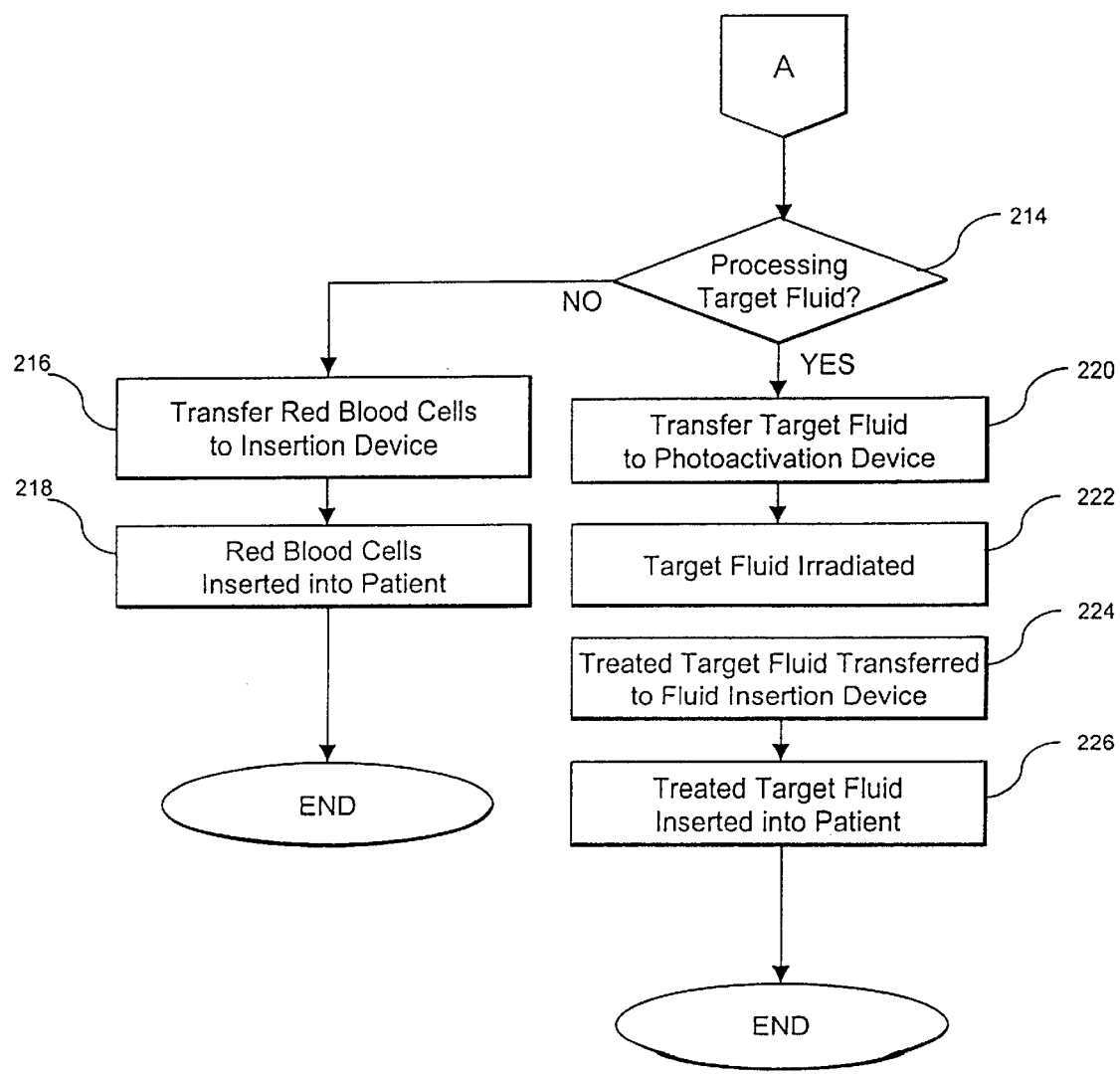

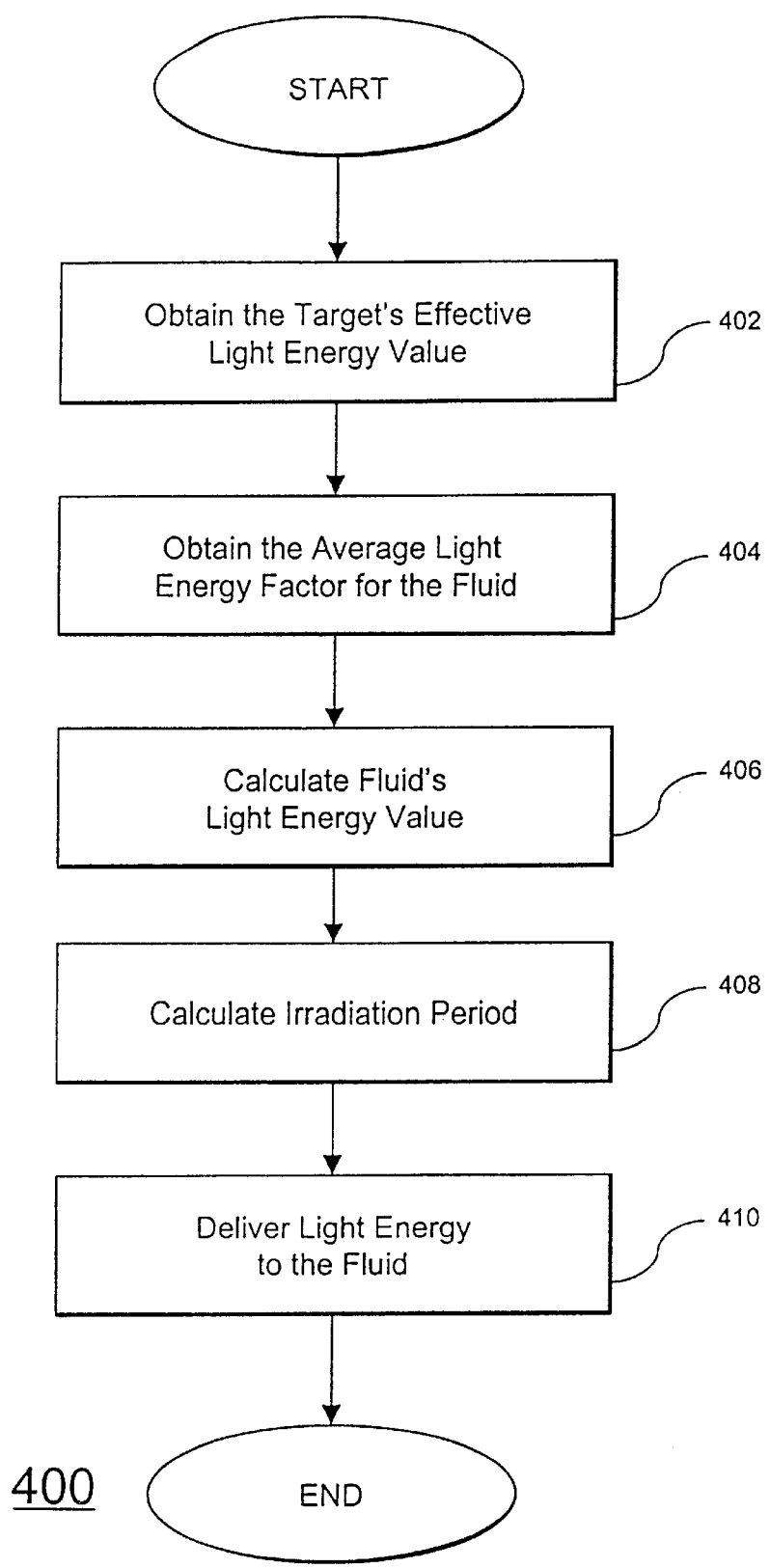

FIG. 5

```
       START
         │
         ▼
┌─────────────────────┐
│ Obtain the Desired  │──── 502
│ Result              │
└─────────────────────┘
         │
         ▼
┌─────────────────────┐
│ Place Target in     │──── 504
│ Non-Attenuating     │
│ Medium              │
└─────────────────────┘
         │
         ▼
┌─────────────────────┐
│ Produce Desired     │──── 506
│ Result              │
└─────────────────────┘
         │
         ▼
┌─────────────────────┐
│ Identify TELEV that │──── 508
│ Produced the        │
│ Desired Result      │
└─────────────────────┘
         │
         ▼
        END
```

500

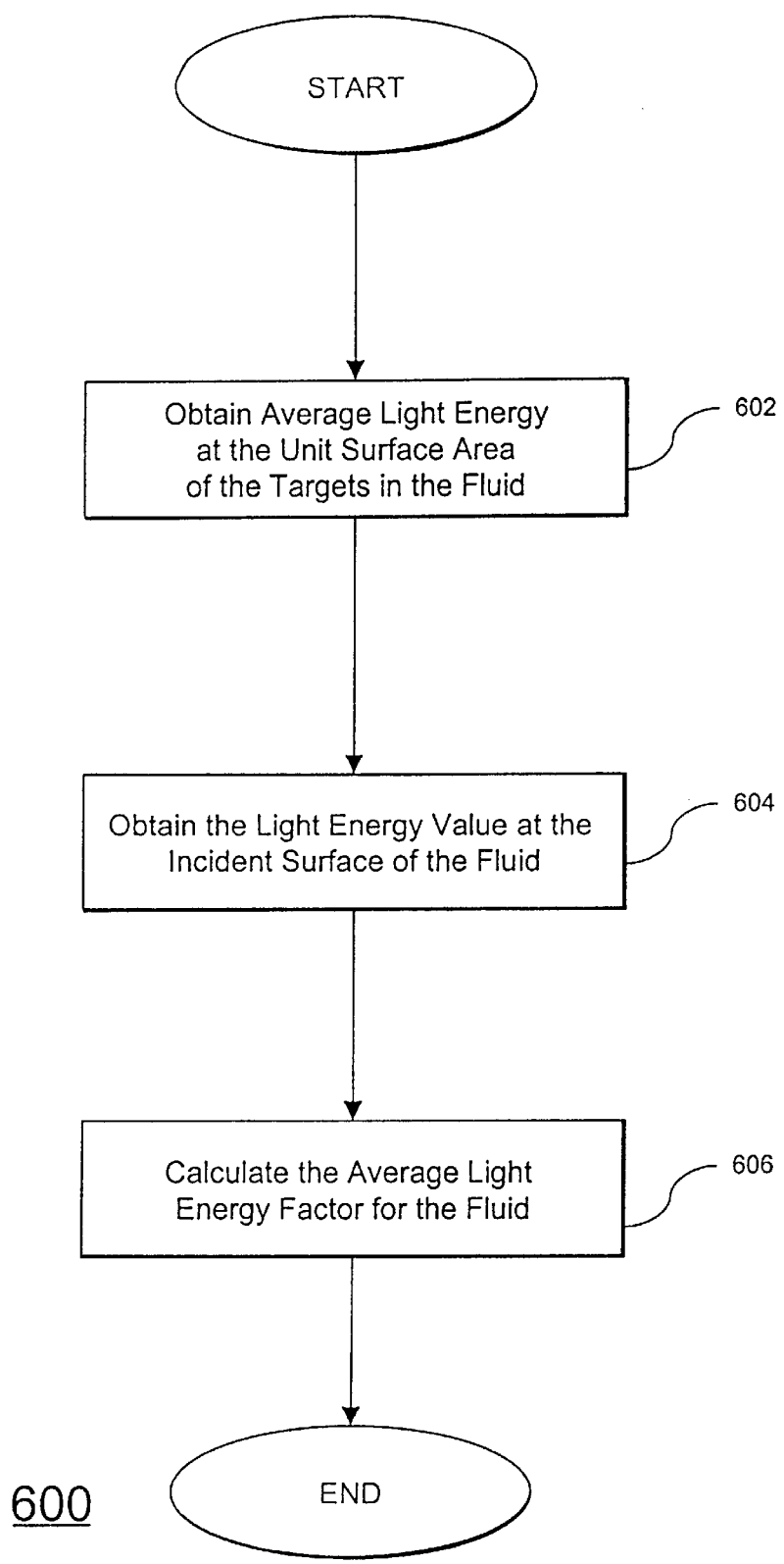

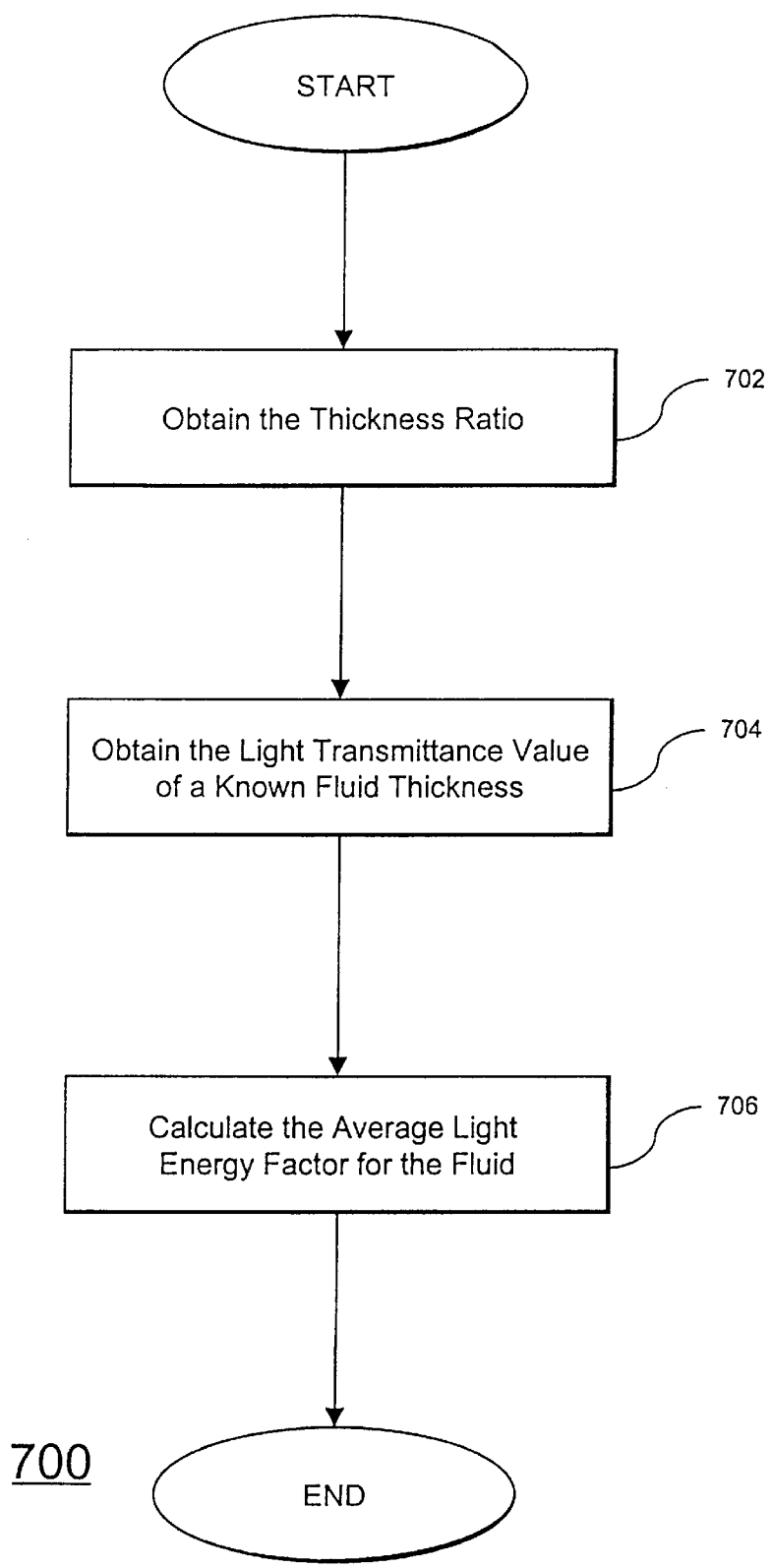

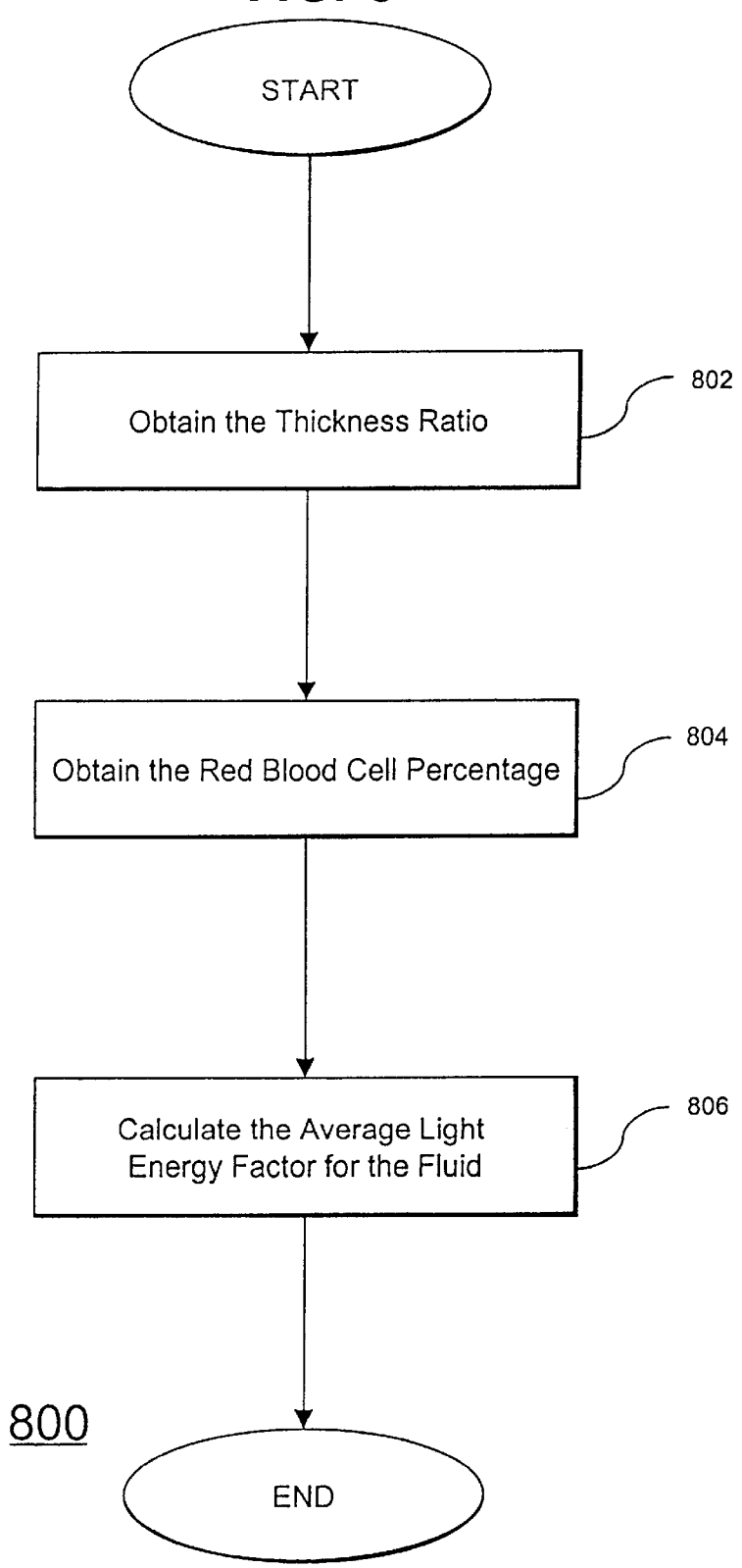

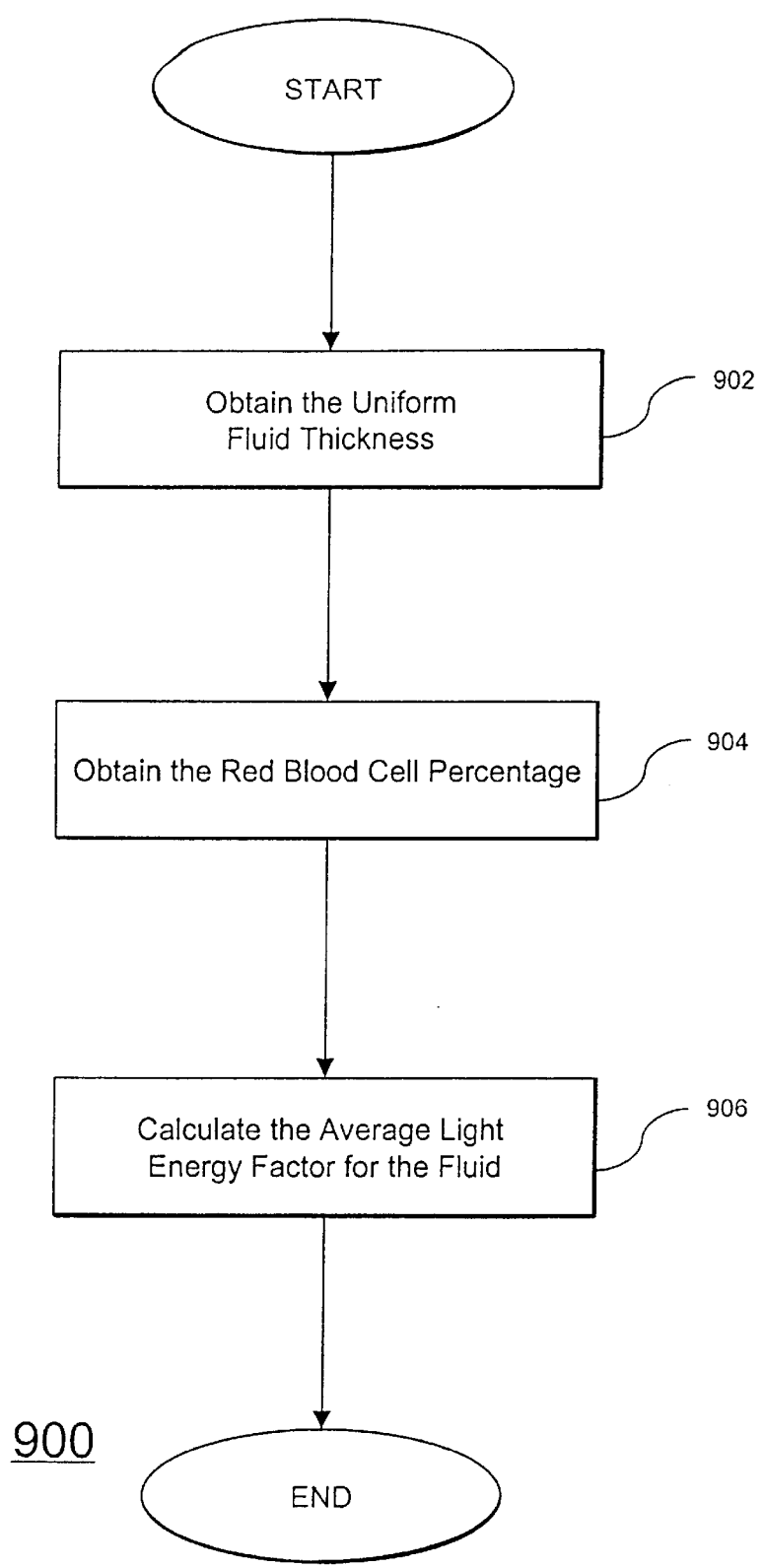

ALE FACTORS

FIG. 11

| Lamp Life Time (Hrs) | L Values |
|---|---|
| 0-9 | 8605, 7855, 7625, 7488, 7390, 7313, 7249, 7195, 7147, 7105 |
| 10-19 | 7067, 7032, 7000, 6970, 6942, 6916, 6892, 6869, 6847, 6826 |
| 20-29 | 6806, 6787, 6769, 6751, 6734, 6718, 6702, 6687, 6672, 6658 |
| 30-39 | 6644, 6630, 6617, 6604, 6592, 6580, 6568, 6556, 6545, 6534 |
| 40-49 | 6523, 6512, 6502, 6491, 6481, 6472, 6462, 6452, 6443, 6434 |
| 50-59 | 6425, 6416, 6407, 6399, 6390, 6382, 6374, 6366, 6358, 6350 |
| 60-69 | 6342, 6334, 6327, 6319, 6312, 6305, 6297, 6290, 6283, 6276 |
| 70-79 | 6269, 6263, 6256, 6249, 6243, 6236, 6230, 6223, 6217, 6211 |
| 80-89 | 6205, 6198, 6192, 6186, 6180, 6174, 6169, 6163, 6157, 6151 |
| 90-99 | 6146, 6140, 6135, 6129, 6124, 6118, 6113, 6107, 6102, 6097 |
| 100-109 | 6092, 6087, 6081, 6076, 6071, 6066, 6061, 6056, 6051, 6047 |
| 110-119 | 6042, 6037, 6032, 6027, 6023, 6018, 6013, 6009, 6004, 5999 |
| 120-129 | 5995, 5990, 5986, 5981, 5977, 5973, 5968, 5964, 5960, 5955 |
| 130-139 | 5951, 5947, 5942, 5938, 5934, 5930, 5926, 5922, 5918, 5913 |
| 140-149 | 5909, 5905, 5901, 5897, 5893, 5889, 5885, 5882, 5878, 5874 |
| 150 | 5870 |

AVERAGE SINGLE LAMP IRRADIANCE AT 25 cm

METHOD AND SYSTEM FOR DETERMINING AN EFFECTIVE AMOUNT OF LIGHT ENERGY TO DELIVERY TO FLUIDS HAVING TARGETS FOR THE LIGHT ENERGY

FIELD OF THE INVENTION

This invention generally relates to determining an amount of light energy to deliver to fluids, particularly partially transparent fluids, containing targets for the light energy, in order to deliver an effective amount of light energy to the targets. The invention particularly relates to phototherapy and photopheresis systems where an effective amount of light energy is desired to be delivered to targets in biological fluids.

BACKGROUND OF THE INVENTION

Light irradiation or phototherapy has been widely used in the chemical and biological sciences for many years. Ultraviolet (UV) light irradiation of blood was used in the 1930's, 40's, and 50's for the treatment of many conditions. These conditions included bacterial diseases such as septicemias, pneumonias, peritonitis, wound infection, viral infections including acute and chronic hepatitis, poliomyelitis, measles, mumps, and mononucleosis. Phototherapy or light irradiation also includes the processes of exposing photoactivatable or photosensitizable targets, such as cells, blood products, bodily fluids, chemical molecules, tissues, viruses, and drug compounds, to light energy, which induces an alteration in or to the targets. In recent years, the applications of phototherapy are increasing in the medical field. These applications include the inactivation of viruses contaminating blood or blood products, the preventive treatment of platelet-concentrate infusion-induced alloinmunization reactions, and the treatment of both autoimmune and T-cell mediated diseases. Light irradiation applications also include the irradiation sterilization of fluids that contain undesirable microorganisms, such as bacteria or viruses.

Numerous human disease states, particularly those relating to biological fluids such as blood, respond favorably to treatment by visible or UV light irradiation. Light irradiation may be effective to eliminate immunogenicity in cells, inactivate or kill selected cells, inactivate viruses or bacteria, or activate desirable immune responses. For example; phototherapy can be used as an antiviral treatment for certain blood components or whole blood. (See PCT Application WO 97/36634 entitled Photopheresis Treatment of Chronic HCV Infections). In this case, a pathogenic virus in a donated platelet concentrate can be inactivated by UV light exposure.

Indeed, certain forms of light irradiation may be effective by themselves, without the introduction of outside agents or compounds, while others may involve the introduction of specific agents or catalysts. Among the latter treatment techniques is the use of photoactivatable drugs. In a particular application, it is well known that a number of human disease states may be characterized by the overproduction of certain types of leukocytes, including lymphocytes, in comparison to other population of cells which normally comprise whole blood. Excessive abnormal lymphocyte populations result in numerous adverse effects in patients including the functional impairment of bodily organs, leukocyte mediated autoimmune diseases and leukemia related disorders many of which often ultimately result in fatality.

Uses of photoactivatable drugs may involve treating the blood of a diseased patient where specific blood cells have become pathogenic as a consequence of the disease state. The methods generally may involve treating the pathogenic blood cells, such as lymphocytes, with a photoactivatable drug, such as a psoralen, which is capable of forming photoadducts with lymphocyte DNA when exposed to UV radiation.

A specific type of phototherapy is extracorporeal photopheresis (ECP). An application of ECP is for the treatment of cutaneous T-cell lymphoma (CTCL). In an example of this therapy, 8-methoxypsoralen (8-MOP), a naturally occurring light-sensitive compound, is orally administrated to a patient prior to before ECP treatment. During the ECP treatment, blood is withdrawn from the patient, anticoagulated, and the white cells are separated by centrifugation and collected as a leukocyte enriched fraction, also known as the buffy coat. The 8-MOP molecules in the blood enter the white blood cell nuclei and intercalate in its double-stranded DNA helix.

In the extracorporeal circuit, UV light is directed at the leukocyte-enriched blood fraction and promotes the photoactivation of the target 8-MOP molecules. The photoactivated 8-MOPs alter the pathogenic leukocyte by cross-linking to the thymidine bases and prevent the unwinding of DNA during transcription. The fluid containing the altered leukocytes is then reinfused back into the patient. The reinfusion induces a therapeutically significant delayed immune attack that targets antigens on the surface of both irradiated and unirradiated leukocytes of the same pathogenic clones. See PCT Application WO 97/36581 entitled Photopheresis Treatment of Leukocytes, which is expressly hereby incorporated herein by reference in its entirety. This PCT Application discloses the UVAR® system for ECP. U.S. Pat. Nos. 4,321,919, 4,398,906, 4,428,744, and 4,464, 166, each of which is expressly hereby incorporated herein by reference in its entirety, also describe, inter alia, methods for reducing the functioning lymphocyte population of a human subject using photopheretic techniques.

ECP also has been shown to be an effective therapy in a number of autoimmune diseases such as progressive systemic sclerosis (see A. H. Rook et al., ARCH. DERMATOL. 128:337–346 (1992)), inflammatory bowel disease, rheumatoid arthritis (see S. Malawista, et al., ARTHRITIS RHEUM. 34:646–654 (1991)), and juvenile onset diabetes mellitus (see J. Ludvigsson, DIABETES METAB. REV. 9(4):329–336 (1993)), as well as other T-cell mediated phenomena including graft-versus-host disease (see Rosseti et al., TRANSPLANT 59(1):149–151 (1995)), and organ allograft rejection after transplantation (see A. H. Rook, et al., J. CLIN. APHERESIS 9(1):28–30 (1994)). The ECP treatment preferably results in a highly specific immune response against aberrant T-cells as well as removal of pathogenic antibodies and circulating immune complexes.

A difficulty inherent in light irradiation or phototherapy techniques when used in the irradiation of fluids and/or their target components, however, is that often times the fluid is not completely transparent to light, e.g., the fluid itself is not entirely transparent and/or the fluid contains material (e.g., non-target material) that is not entirely transparent to light. Material that is not completely transparent to light energy attenuates the irradiance of the light. This phenomenon is particularly undesirable in phototherapy or photopheresis applications since some targets in the fluid will receive light that is attenuated by the nontransparent material. This attenuation makes it difficult to predict how much light energy should be delivered to the fluid to provide a desired amount of light energy to targets in the fluid.

Another source of light attenuation in fluids is stacking. Stacking occurs in a fluid when material or targets in the fluid are not distributed uniformly on the fluid surface but rather are located at different depths throughout the fluid. Therefore, for instance, targets in the outer most layer of the fluid, closest to the irradiating light source, may be exposed to incident light intensity, while the targets below the surface layer may receive attenuated light energy.

Furthermore, the shapes of non-transparent material in the fluid and their alignment can be a cause of light attenuation. For example, in photopheresis applications, non-targets in he biological fluid may include red blood cells, which have discord shapes with depressions at the middle. When red blood cells are aligned parallel to the light energy source during irradiation, their attenuation of light is minimized. However, when red blood cells are aligned perpendicular to the light energy source during irradiation, their attenuation of light is maximized. Since the alignment of such fluid material is usually not predictable, it is presently difficult to accurately determine how much light energy should be delivered to the biological fluid in order to deliver a desired amount of light energy to each target in the fluid and overcome the light attenuation caused by the alignment of the material.

The CTCL ECP methodology referenced in PCT Application WO 97/36581 can be used to illustrate these exemplary light attenuation characteristics. The buffy coat suspension usually contains some red blood cells and platelets due to inefficiencies inherent in the cell separation techniques utilized. Since the buffy coat suspension, red blood cells and platelets are not completely transparent, they can attenuate the light energy during irradiation. Also, since the fluid's thickness during irradiation can support target white blood cells at different depths, stacking is present. Finally, the alignment of red blood cells in the fluid containing the buffy coat may attenuate the light energy.

With CTCL ECP, the desired amount of light energy for delivery to targets may be result-based, e.g., delivering enough light energy to the target white blood cells to produce a gradual death rate culminating in at least fifty (50) percent of treated, irradiated white blood cells dead after day six (6) of irradiation. Yet, the fluid's non-transparent qualities presently make it difficult to accurately calculate the amount of light energy required to deliver to the fluid, in order to achieve the desired result.

A conventional way to reduce the effect of the attenuation of light in such applications is to constantly agitate the fluid during irradiation. Agitation assists to produce uniform exposure of the targets to the light energy, yet it does not directly address all the light attenuating factors present in such applications. See PCT Application WO 98/22164, entitled Blood Product Irradiation Device Incorporating Agitation, which is expressly incorporated herein by reference.

It is therefore desirable to have a system for determining an effective amount of light energy to deliver to fluids containing targets for the light energy, in order to deliver an effective amount of light energy to the targets and, more particularly, to have a system applicable to phototherapy and photopheresis systems for determining an effective amount of light energy to deliver to a biological fluid containing targets for the light energy where an effective amount of light energy is desired to be delivered to the targets.

SUMMARY OF THE INVENTION

The present invention relates to methods and systems for determining the effective amount of light energy for delivery to a fluid containing targets, and delivering said light energy to the targets. In a specific embodiment, the fluid is a biological fluid. Specifically, the fluid light energy value (FLEV) may be calculated by obtaining the target's effective light energy value (TELEV) and the average light energy factor of the fluid (ALE Factor). In a specific embodiment, a computer processor may be used to determine the FLEV.

In a specific embodiment, the fluid containing the targets is a biological fluid. More preferably, the biological fluid comprises leukocyte-rich buffy coat. The leukocyte-rich buffy coat may be treated with a light energy activatable drug. More preferably, the buffy coat may be treated with 8-MOP. In another embodiment of the present invention, the fluid is a homogenous biological fluid. The biological fluid may also comprise non-target materials. These non-target materials may attenuate the light energy, and affect calculation of the FLEV. Non-target materials may consist of red blood cells. Further, the light energy delivered to the targets may be UV light energy. More preferably, the light energy is ultraviolet A (UVA) light energy.

In a specific embodiment, the effective light energy value of the targets may be obtained by accessing an effective light energy value table. In another embodiment, the effective light energy value of the targets may be obtained by placing the targets in fluid and irradiating the fluid with sample light energy values. The selected fluid may limit the attenuation of the delivered light energy. In a specific embodiment, the fluid may consist of saline. More specifically, leukocyte-rich buffy coat targets may be placed in saline and irradiated to identify a light energy value whereby a desired percentage of the leukocytes will gradually die over the course of a specified time after exposure to the light energy. In yet another embodiment, the selected fluid may consist of plasma. Sample biological fluids may be obtained from donors. The targets in the sample fluids may then be irradiated with sample light energy values to identify the effective light energy value. In a specific embodiment, a computer processor may be used to determine the effective light energy value of the targets.

The fluid's average light energy factor may be determined by accessing a light energy factor table. In a specific embodiment, a computer processor may be used to determine the average light energy factor.

In another embodiment of the present invention, the average light energy factor may be calculated from the measurements of an average light energy value at a unit surface area of the targets in the biological fluid and a light energy value at an incident surface of the biological fluid film. In a specific embodiment, the average light energy at unit surface area of the targets in the biological fluid may be obtained by accessing an average light energy at unit surface area table. The light energy value at an incident surface may also be obtained by accessing a light energy value at an incident surface table. These values may also be directly calculated.

In a further embodiment, the average light energy factor may be calculated from the measurements of a thickness ratio and a light transmittance value of a known fluid thickness. The thickness ratio may be obtained by accessing a thickness ratio table. The irradiation period may be obtained by accessing a light transmittance value of a known fluid thickness. In another embodiment, the thickness ratio may be calculated from the uniform thickness for said biological fluid and the thickness for said non-targets. Further, the uniform thickness for the biological fluid may be obtained by accessing a uniform thickness table, while the thickness for non-targets may be obtained by accessing a non-target thickness table.

In another embodiment of the present invention, the average light energy factor may be calculated from the measurements of a thickness ratio and the red blood cell percentage of the biological fluid. The red blood cell percentage may be obtained by accessing a red blood cell percentage table.

Another method for calculating the average light energy factor may utilize the measurements of the uniform thickness of the biological fluid and the red blood cell percentage of the biological fluid. The equations used in this method may preferably be used for red blood cell concentrations in the biological fluid of up to about twenty (20) percent, and more preferably for red blood cell concentrations of up to about seven (7) to eight (8) percent.

In one embodiment, theoretical stacking of red blood cells may not occur. In another embodiment, stacking of red blood cells may occur and a factor may be obtained. This factor may, in a particular embodiment, be between 1 and 2, and more particularly about 1.5.

In a further embodiment, the irradiation time period required by a light energy source to deliver the FLEV may be calculated once the target's effective light energy value and the fluid's average light energy factor have been determined using one of the methods of the present invention and used to calculate the FLEV. The irradiation time period may be calculated from measurements of a volume of biological fluid value, a percent of red blood cells value and a decay life value.

In another embodiment of the present invention, a computer system may be used to determine the FLEV. This computer system may comprise a processor, memory and a computer process. More specifically, the computer process may comprise an obtainer configured to obtain the effective light energy value of the target, an obtainer configured to obtain the average light energy factor of the fluid and/or a calculator configured to calculate the FLEV. In a specific embodiment, the calculator used to calculate the FLEV may also be configured to calculate an irradiation time period over which the FLEV is delivered to the targets. The calculator used to calculate the FLEV may also contain an obtainer to obtain a decay life value for the light energy source. The calculator may also contain an obtainer to obtain a volume of biological fluid value and an obtainer to obtain a percent of red blood cells value.

In a specific embodiment, the obtainer configured to obtain the effective light energy value of the targets may include an accessor configured to access a light energy factor table. In another embodiment, the obtainer configured to obtain the effective light energy value of the targets may include an obtainer configured to obtain the average light energy value at a unit surface area of the targets, an obtainer configured to obtain a light energy value at an incident surface of the biological fluid and/or a calculator configured to calculate the average light energy factor. More preferably, the obtainer configured to obtain a light energy value at an incident surface of the biological fluid may contain an accessor configured to access an average light energy value at an incident surface of the biological fluid table, and/or an accessor configured to access an average light energy value at unit surface area table.

The obtainer configured to obtain an average light energy factor may contain an obtainer configured to obtain a thickness ratio, an obtainer configured to obtain a light transmittance value of a known fluid thickness and/or a calculator configured to calculate the average light energy factor for the biological fluid. More preferably, the obtainer configured to obtain a thickness ratio may contain an accessor configured to access a thickness ratio table, and the obtainer configured to obtain a light transmittance value of a known fluid thickness may contain an accessor configured to access a light transmittance value of a known fluid thickness table.

In a further embodiment, the obtainer configured to obtain the thickness ratio may include an obtainer configured to obtain a uniform thickness for the biological fluid, an obtainer configured to obtain a thickness for the non-targets and/or a calculator configured to calculate the thickness ratio. More preferably, the obtainer configured to obtain a uniform thickness for the biological fluid may contain an accessor configured to access a uniform thickness table, and the obtainer configured to obtain a thickness for the non-targets may contain an accessor configured to access a non-target thickness table.

In a further embodiment, the obtainer configured to obtain the average light energy factor may include an obtainer configured to obtain a red blood cell percentage for the biological fluid. More preferably, the obtainer configured to obtain a red blood cell percentage may contain an accessor configured to access a red blood cell percentage table.

In another embodiment of the present invention, the obtainer configured to obtain the thickness ratio may include an obtainer configured to obtain a uniform thickness for the biological fluid, an obtainer configured to obtain a thickness for the non-targets and a calculator configured to calculate the thickness ratio. More preferably, the obtainer configured to obtain the uniform thickness may contain an accessor configured to access a uniform thickness table, and the obtainer configured to obtain the thickness of the non-targets may contain an accessor configured to access a non-target thickness table.

In a further embodiment, the obtainer configured to obtain the average light energy factor may include an obtainer configured to obtain a red blood cell percentage for the biological fluid. The computer system may further include an obtainer configured to obtain the red blood cell stacking factor. In a particular embodiment, the stacking factor may be between 1 and 2. More particularly, the stacking factor may be 1.5.

The present invention also relates to a computer readable medium containing instructions for controlling a computer system used to perform the methods described herein for determining a fluid light energy value for delivery to a biological fluid comprising targets, wherein an effective amount of light energy is delivered to the targets.

Methods and articles of manufacture consistent with the present invention may involve the functions and operations performed by the described systems and the components thereof.

Other objectives, features, and advantages of the present invention will become apparent from the following detailed description. The detailed description and the specific examples, while indicating specific embodiments of the invention, are provided by way of illustration only. Accordingly, the present invention also includes those various changes and modifications within the spirit and scope of the invention that may become apparent to those skilled in the art from this detailed description.

BRIEF DESCRIPTION OF THE FIGURES

The accompanying figures, which are incorporated in and constitute a part of the specification, illustrate embodiments of the invention and, together with the description, serve to explain the objects, advantages and principles of the invention.

FIGS. 2A and 2B are a flow diagram 200 of the steps performed by a photopheresis system according to an implementation of the present invention.

FIG. 4 is a flow diagram 400 of the steps performed by the photoactivation program 314 when requested to deliver light energy to fluid according to an implementation of the present invention.

FIG. 5 is a flow diagram 500 of the steps performed by the photoactivation program 314 when calculating the target's effective light energy value according to an implementation of the present invention.

FIG. 6 is a flow diagram 600 of the steps performed by the photoactivation program 314 when calculating the average light energy factor for the fluid according to an implementation of the present invention.

FIG. 7 is a flow diagram 700 of the steps performed by the photoactivation program 314 when using an analytical equation to calculate the average light energy factor for the fluid according to an implementation of the present invention.

FIG. 8 is a flow diagram 800 of the steps performed by the photoactivation program 314 when using calculate the average light energy factor for fluids containing red blood cells as non-target according to an implementation of the present invention.

FIG. 9 is a flow diagram 900 of the steps performed by the photoactivation program 314 when using a stacking equation to calculate the average light energy factor for the fluid according implementation of the present invention.

FIG. 11 is a table providing an exemplary single lamp decay value over time.

DETAILED DESCRIPTION OF THE INVENTION

Figure 1:
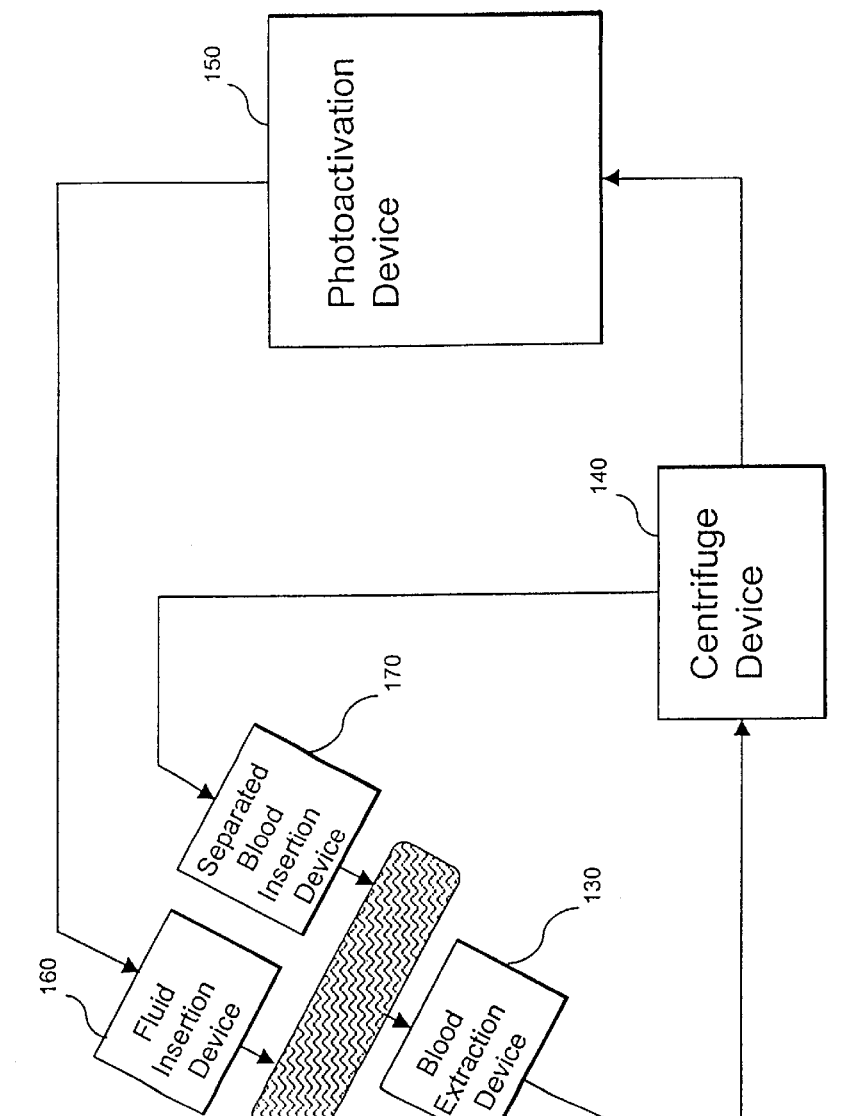
FIG. 1 is a diagram 100 of a photopheresis system according to an implementation of the present invention.

The following definitions are not meant to be limiting in nature and serve to provide a clearer understanding of certain aspects of the present invention.

Definitions:

Target—Targets include photosensitive or photoactivatable materials that undergo a change when exposed to light energy. Accordingly, targets maybe manipulated, altered, stimulated and/or activated when exposed to light energy. Targets include, but are not limited to, biological targets such as red blood cells, white blood cells, platelets, protein factors, viruses, bacteria, parasites, DNA, RNA, toxins, and drug compounds. Targets exposed to light energy may also interact with other materials or targets.

Phototherapy—Phototherapy includes procedures where photosensitive, photochangeable or photoactivatable targets are exposed to light energy.

Fluid—Fluids include substances that may be used as carriers of targets. Examples of fluid include spinal fluid, cells, and other fluids compatible with a target such as phosphate buffered saline, plasma, etc., and combinations thereof. The fluid may include non-targets and may be biological in nature.

Non-target—Non-targets include material that attenuates light energy, yet are not the intended targets for light energy. Non-targets include red blood cells and platelets.

Biological Fluid—Biological fluids include fluids that carry targets and/or non-targets and that have the capacity to support biological targets. Biological fluids may include whole blood, plasma, synovial fluid, amniotic fluid, and spinal fluid, in addition to carriers such as saline or other known media, preferably compatible with biological organisms such as cells and tissues, and combinations thereof.

Photopheresis—A type of phototherapy in which fluid is extracted from a donor, exposed to light energy, and returned to the donor. In a particular embodiment, the extracted fluid, such as whole blood or portions of whole blood (such as buffy coat), may contain targets. CTCL ECP is an example of photopheresis.

Photoactivation—Photoactivation is a process in which a target is changed (e.g., manipulated, altered, stimulated, or activated) by exposure to light energy. An example of a target undergoing photoactivation is the drug 8-MOP used in CTCL ECP which, previous to photoactivation, is inert. Exposing this drug compound to light energy activates it to a form that can cross-link lymphocyte DNA.

Light Energy—Light energy is the form of energy that reacts with targets, such as biological or chemical targets. An example of light energy used in phototherapy applications is UV light and, more specifically, UVA light in CTCL ECP methodology.

Desired Result—A desired result is an outcome for light energy manipulated targets. In the CTCL ECP context, for example, a desired result might be to have a specific percentage of irradiated leukocytes gradually die over a specific time period after exposure to the light energy.

TELEV—The Targets' Effective Light Energy Value is the light energy value delivered to the targets, preferably calculated in a medium or fluid that contains essentially no other light attenuating material, that produces a desired result.

ALE Factor—The Average Light Energy Factor compares the amount of light energy present at the incident surface of the fluid with the amount of light energy at the surface of the targets within the fluid.

FLEV—The Fluid's Light Energy Value is the amount of light energy delivered to the fluid to maximize the probability that targets receive their TELEV.

Uniform Fluid Thickness—Uniform fluid thickness is the fluid thickness where the light irradiation of targets occurs.

Non-Target Thickness—The non-target thickness is the thickness of the non-target material that is the dominant light attenuating non-target material in a fluid.

Thickness Ratio—The thickness ratio is the ratio of the uniform thickness of the fluid to the average thickness of non-targets in the fluid.

Irradiation Period—Irradiation period is the time period that the light energy source irradiates the fluid containing the targets.

Reference will now be made in detail to implementations of the present invention as illustrated in the accompanying drawings. Wherever possible, the same reference numbers will be used throughout the drawings and the following description to refer to the same or like parts.

Light irradiation methodologies, as discussed above, involve the delivery of light energy to a target to achieve a desired result. The targets may be carried in a medium (e.g., a fluid) during light irradiation. In a particular context of the present invention, the amount of light energy delivered to targets in a fluid that contains essentially no non-target light attenuating material, in order to achieve the desired result, is the TELEV. Indeed, non-target materials may also be present in the fluid, which may result in the attenuation of the light energy that is desired to be delivered to the targets. Accordingly, the present invention, inter alia, accounts for the light attenuation of the non-target material present in the fluid by determining the FLEV so that the TELEV may be delivered to the target material.

In a specific application of the present invention, phototherapy systems involve irradiating targets, such as cells or a drug within a cell, with light energy. When the targets are microscopic or unable to stand-alone, a carrier fluid may be used to deliver the targets for irradiation.

The amount of light energy required by a target may be based on the result desired. For example, in CTCL ECP it may be desirable to have a certain percentage of the white blood cells die gradually over a specific period of time after light irradiation treatment (e.g., at least fifty (50) percent of the white blood cells gradually die within six (6) days after irradiation). See PCT Application WO 97/36581. This light energy value required to produce a desired result (e.g., a desired percentage of the targets gradually die over a specified time after exposure to light energy) is the TELEV. There are a number of conventional approaches that can be used to obtain the TELEV. Some of these approaches are discussed later in more detail. Indeed, TELEV values may be predetermined and may be available in the memory of a computer system used with the present invention, e.g., in a look-up table.

Since the material in a fluid may attenuate light energy otherwise desired to be delivered to targets in the fluid, the fluid requires additional light energy exposure to maximize the probability that targets in the fluid receive their TELEV. The amount of light energy needed for delivery to the fluid to maximize the probability that the targets receive the TELEV is referred to as the Fluid's Light Energy Value (FLEV). The FLEV is based, in part, on the light attenuation characteristics of the fluid and material therein, and may be determined by the methods and systems of the present invention.

As discussed above, light attenuation in the fluid may occur for numerous reasons. For example, attenuation may occur if the fluid being irradiated contains target and/or non-target material that are not entirely transparent. Also, attenuation may occur if the fluid sample being irradiated supports layers of targets and/or non-targets. In addition, the shape and alignment of the individual targets and/or non-targets may influence the quantity of light attenuation.

In one embodiment of the present invention, the FLEV can be calculated by determining the TELEV and the percent of incident light energy that will be delivered to an average unit area of fluid. This percent is referred to as the fluid's Average Light Energy Factor (ALE Factor). Once the ALE Factor is known, the FLEV can be determined as follows:

$$FLEV = \frac{TELEV}{ALE\text{ Factor}} \tag{1.0}$$

For example, it may be determined that one (1) Joule of UV light energy delivered to targets will produce a desired result (TELEV). However, due to attenuation of the light energy in the fluid (e.g., via the presence of non-transparent material in the medium containing the targets or stacking), the light energy reaching the targets in the fluid is reduced and, thus, approximately 0.1 Joule of UV light energy actually reaches the targets. Thus, the ALE Factor is 0.1, i.e., only ten (10) percent of the light energy delivered to the surface of the fluid will actually reach (on average) all the targets. Thus, applying equation 1.0, 10 Joules (FLEV) of light energy is required to be delivered to the surface of the fluid to ensure that the targets (on average) receive 1 Joule of light energy (the desired result).

In a particular embodiment of the invention, the ALE Factor may be determined by dividing the light energy delivered at the unit surface area of the targets, Ea (Joules/$cm^2$), by the incident light energy delivered at the incident surface of the fluid, Eo (Joules/$cm^2$):

$$\text{ALE Factor}=Ea/Eo \tag{1.1}$$

The following provides exemplary means for determining the ALE Factor, taking into consideration the light attenuating characteristics of the fluid and its components. By way of example, in CTCL ECP applications when a buffy coat suspension with a uniform film thickness (D) is irradiated by an UVA light with an incident irradiance (Io) at the fluid film surface (mW/$cm^2$), the Eo delivered at the fluid surface during a given irradiation period (t) is expressed by equation 1.2:

$$Eo=Io*t \tag{1.2}$$

Buffy coat suspension is partially transparent to the UVA light. Accordingly, this fluid attenuates the irradiance of the light at a given point inside the fluid. The degree of attenuation is a function of absorptivity of the fluid and the light penetration depth from the fluid surface.

Assuming Beer's law, the light transmittance ($T_1$) of the fluid between its incident surface and a given point in the fluid at a distance ($D_1$) can be expressed as:

$$T_1=10\hat{}(-a*c*D_1) \tag{1.3}$$

where a is the light absorptivity of the fluid ($cm^2$/gr) and c is the concentration of UVA absorbing component in the fluid (gr/$cm^3$).

Equation 1.3 can be expressed as:

$$T_n=10\hat{}(-a*c*D_n) \tag{1.4}$$

Where $D_n$ is the distance from the incident surface of the fluid and n is $D_n/D_1$:

$$T_n=(T)^n \tag{1.5}$$

In addition, the irradiance (In) at the distance of $D_n$ from the incident surface is:

$$In=Io*(T_1)^n \tag{1.6}$$

The average irradiance value (Ia) over the whole range of the fluid film thickness ($D_r$) can be calculated by integrating over the range of the fluid depth and dividing it by the film thickness:

$$Ia = Io\left[\left(\frac{1}{N}\right)\int_0^N T_1^n d_n\right] \tag{1.7}$$

where $N=D_r/D_1$ and the ratio of Ia to Io is:

$$Ia/Io = \left[\left(\frac{1}{N}\right)\int_0^N T_1^n d_n\right] \tag{1.8}$$

Integrating over the film thickness the ratio becomes:

$$Ia/Io = \frac{1}{N}\left(\frac{T_1^N - 1}{\ln(T_1)}\right) \quad (1.9)$$

One thus arrives at the following analytical equation:

$$Ea/Eo = \frac{1}{N}\left(\frac{T_1^N - 1}{\ln(T_1)}\right) \quad (2.0)$$

where N is the ratio of the uniform film thickness D (cm) to the non-target non-transparent material thickness $D_1$ (cm), and T1 is the light transmittance of the light through the fluid, when the fluid has a fluid thickness equal to the thickness of the dominant non-target. A non-target is dominant when compared to any other non-targets. It is the predominant light attenuator. The accuracy of this calculation may be maximized in situations where the target and dominant non-target material in the fluid are uniformly distributed throughout the fluid, e.g., by stirring.

Equation 2.0 is particularly applicable to partially transparent fluids and, in particular, can be used in photopheresis applications to estimate the average amount of UVA light energy delivered to white blood cells in a well stirred buffy coat suspension. In a specific embodiment, when the application is used with fluids containing red blood cells (with a thickness of about $2*10^{-4}$ cm) as dominant non-target, light attenuating material, equation 2.0 becomes:

$$Ea/Eo = \frac{1}{N}\left(\frac{\left(1 - \frac{H}{100}\right)^N - 1}{\ln\left(1 - \frac{H}{100}\right)}\right) \quad (2.1)$$

where H is the hematocrit value of the fluid.

An additional exemplary way to determine the ALE Factor, preferably when the fluid comprises a dominant attenuating non-target such as red blood cells, is to use the following stacking equation:

$$Ea/Eo = \frac{1}{Y*C*D} \quad (2.2)$$

where C is the percent of non-targets in the fluid and D (cm) is the fluid thickness. Y is a dimensionless number that represents the geometric shape of the non-target and the stacking factor. The stacking factor is also a dimensionless number that represents the theoretical amount of physical stacking that takes place within the fluid by the non-targets. In ECP applications, for example, the stacking factor may be a number between 1 and 2. Means for obtaining a stacking factor are described in detail supra. When the non-target is geometrically spheroid, the equation for Y is:

$$Y = \frac{(\pi*R^2 + 2*d*R)*S}{2} \quad (2.3)$$

where R (cm) is the average radius of the non-target, d (cm) is the average thickness of the non-target, and S is the stacking factor.

When red blood cells are the dominant attenuating non-target in a buffy coat suspension, equation 2.2 becomes:

$$Ea/Eo = \frac{1}{Y*H*D} \quad (2.4)$$

where H is the hematocrit value for 1 ml of buffy coat suspension.

The following provides an example of how the stacking equation and stacking factor may be derived. Turning to the exemplary CTCL ECP methodology, red blood cells have a diameter of about $8*10^{-4}$ cm and thickness of about $2*10^{-4}$ cm. There are two extreme cases of orderly aligned situations for the red blood cell distribution in the buffy coat suspension. The first is where all RBC's are evenly distributed in the cube and aligned in such a way that their interference to the UVA irradiation is maximized. In another words, the discord sides of all RBC's are in perpendicular position against the incoming UVA light rays. The second is where all RBC's are evenly distributed in the cube and aligned in such way that their interference to UVA irradiance is minimized. In another words, the discord sides of all RBC's are in parallel position against the incoming UVA light rays.

In the CTCL ECP context, RBC's are preferably randomly distributed in the suspension and the effect of the interference could be somewhere between these two theoretical situations. Here, a one cubic centimeter (or unit volume) of well-mixed buffy coat suspension with UVA light irradiated on one side only is considered. In addition, in these two cases it was assumed that no RBC's were stacked against each other, i.e. no rouleaux formation, because of low hematocrit in buffy coat suspensions.

Considering a situation where light interference by RBC's is maximized, each cubic centimeter (ml) of the buffy coat suspension could be sliced into 1/d slices where d is the thickness of the red blood cells. Accordingly, the number of RBC's in each slice is:

$$Ns=C/(1/d)=C*d \quad (2.5)$$

where C is the RBC concentration (number of cells/ml) in the buffy coat suspension. Thus, the maximum possible fractional area (Fa) that could block UVA irradiation in a given slice is:

$$Fa=Ns*\pi*R^2=C*d*\pi*R^2 \quad (2.6)$$

where R is the radius of the RBC.

The theoretically minimum number of slices that is required to block the UVA light completely in one square centimeter of irradiated surface area thus is 1/Fa. In order to achieve this, no red blood cell should be shielded behind another red blood cell. The total number of the slices in the cube is 1/d. Therefore, in one cubic centimeter volume of the buffy coat suspension, there are (1/d)/(1/Fa) times of (1/Fa) slices. It follows that one cubic centimeter (or unit volume) of buffy coat suspension contains a total number of slices that can theoretically shield (1/d)/(1/Fa) times of one square centimeter area (or unit area) from the UVA light. Substituting for Fa in equation 2.6:

$$(1/d)/(1/Fa)=Fa/d=C*\pi*R^2 \quad (2.7)$$

In this instance, no red blood cells are shielding other red blood cells from UVA light. For example, if the hematocrit is 5%, the first slice will block 5% of the UVA irradiation and the second slice will block additional 5%, and so on. The last layer in the 1/Fa slices will block the last remaining 5% of the UVA light, thereby blocking the light completely.

Under this condition about slightly less than half of the fluid, including the target cells within, is irradiated by the UVA light; the remaining portion of the fluid is shielded from the light by the red blood cells.

Another situation is where all red blood cells in a slice are located behind other red blood cells in the slice in front of it. For instance, if the hematocrit is 5%, only 95% of the first slice will pass the light. Since all red blood cells in the second and slices behind it are all located behind the red blood cells in the first layer, there is no further blocking of the light and 95% of all fluid in (1/Fa) slices, almost twice as much as the former case, will receive the UVA irradiation. Therefore, incorporating a simple stacking factor (S), equation 2.7 can be rewritten as:

$$(1/d)/(1/\text{Fa}) = \text{Fa}/d = C^*\pi^*R^2{}^*S \qquad (2.8)$$

The value of the stacking factor, S, in ECP applications, thus may be between one and two.

Following a similar analysis, equation 2.8 becomes:

$$(1/d')/(1/\text{Fa}') = \text{Fa}'/d' = C^*2^*d^*R^*S \qquad (2.9)$$

where $d' = 2^*R$.

Equations 2.8 and 2.9 represent two opposite extreme cases of RBC light attenuation. In practice, RBC attenuation of light is somewhere between these two extremes. If we take the average of these extreme cases as an estimate for the situation in practice, the equation becomes:

$$(\text{Fa}/d)\text{ave} = ((\text{Fa}/d) + (\text{Fa}'/d'))/2 = C^*((\pi^*R^2) + (2^*d^*R))^* S/2 \qquad (3.0)$$

For human blood buffy coat suspensions we can approximate $R = 4*10^{-4}$ cm and $d = 2*10^{-4}$ cm for red blood cells. Accordingly, equation 3.0 becomes:

$$(\text{Fa}/d)\text{ave} = 33.12^*C^*S^*10^{-8} \qquad (3.1)$$

Equation 3.1 represents multiples of number of slices, which can block completely the incoming UVA light through one square centimeter area, in one cubic centimeter volume. Assuming the buffy coat suspension inside this one cubic centimeter volume (or unit volume) is well mixed, the UVA energy delivered to the target cells through the one square centimeter (or unit area) window may be expressed as:

$$Ea = Ev/(\text{Fa}/d)\text{ave} = Ev/(33.12^*C^*S^*10^{-8}) \qquad (3.2)$$

where $Ea$ = UVA energy delivered per unit area, Joules/cm²

$Ev = Eo^*A/V$, UVA energy delivered per unit volume, Joules/ml $Eo = Io^*t$, Incident UVA energy delivered per unit area, Joules/cm²

$Io$ = Incident irradiance, Joules/cm²-sec.

$t$ = Irradiation time, seconds.

$V = A^*D$, Irradiated volume, ml.

$A$ = Irradiation area, cm²

$D$ = Buffy coat film thickness, cm $C$ = Red blood cell concentration, $\sim 1.1^*H^*10^8$ cells/ml $H$ = Hematocrit of the buffy coat suspension, %

$S$ = Stacking factor, dimensionless number between 1 and 2.

Substituting $S = 1.5$, the average of 1 and 2, as an estimate and $C = 1.1^*H^*10^8$, equation 3.2 becomes:

$$Ea = Ev/(54.65^*H) \qquad (3.3)$$

Substituting $Ev = Eo^*A/V$ and $V = A^*D$:

$$\frac{Ea}{Eo} = \frac{1}{(54.65 * H * D)} \qquad (3.4)$$

Figure 10:
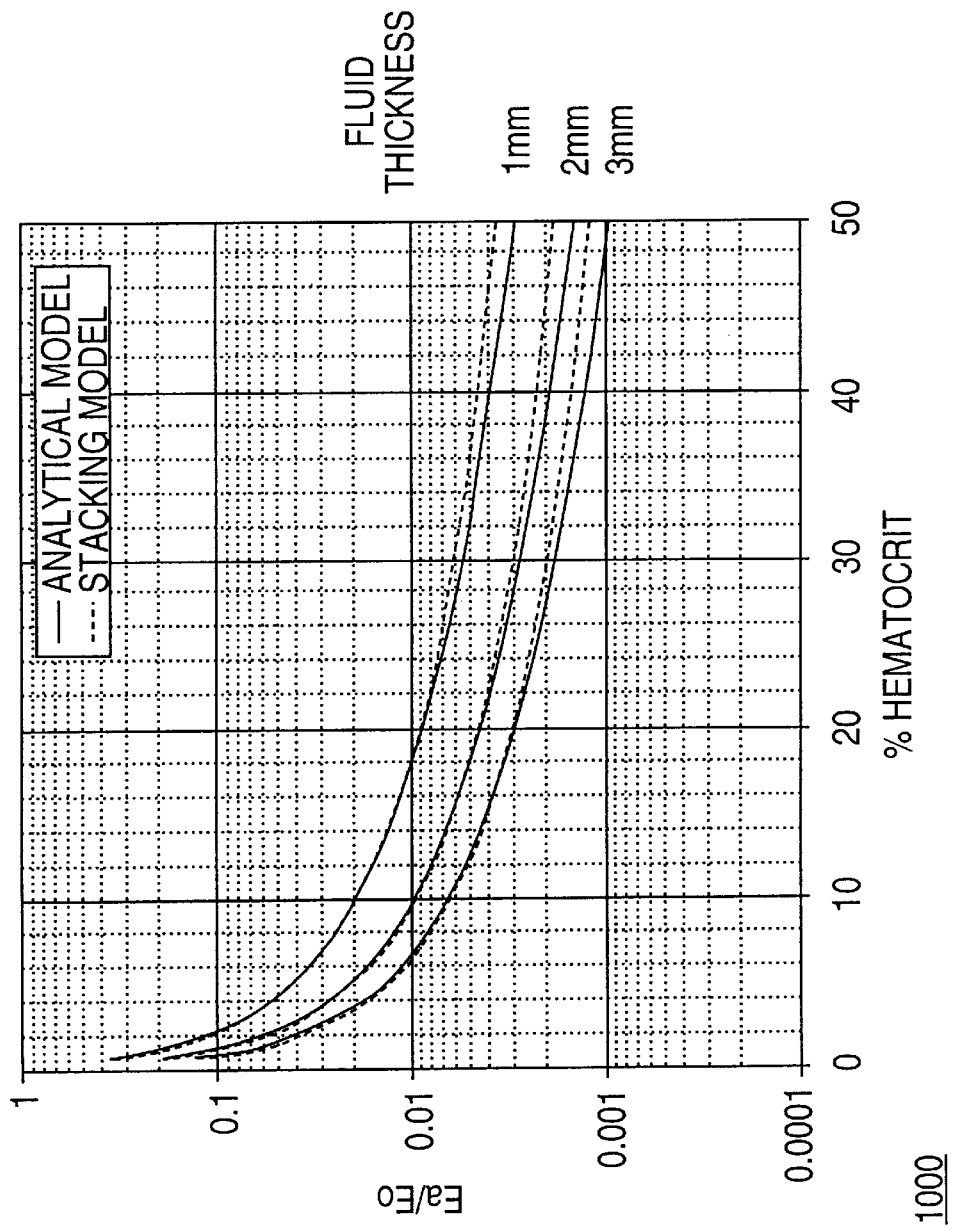
FIG. 10 is a graph of the average light energy factors as a function of percent hematocrit at different fluid thicknesses according to an implementation of the present invention.

Equations 2.0 and 2.4, when applied to a fluid containing red blood cells as the dominant attenuating material, predict almost identical ALE factors up to a red blood cell concentration of about 20%, as represented in FIG. 10. At higher red blood cell concentrations, where the theoretical condition assumed in the stacking equation deviates further from the real situation, the difference between the two equations becomes predictably greater. Indeed, at red blood cell concentrations of over 20% it may be more appropriate to use equation 2.0. At extremely low red blood cell concentrations (e.g., less than 0.2%), where the attenuation caused by the plasma component of the suspension itself is no longer negligible in comparison with the attenuation produced by the red blood cells, equation 3.4 may lose some of its accuracy.

Another method for calculating the ALE Factor may utilize the measurements of the uniform thickness of the biological fluid and the red blood cell percentage of the biological fluid. The equations used for this method can be preferably utilized with red blood cell concentrations in the buffy coat suspension of up to twenty (20) percent, and most preferably used with a red blood cell concentration of up to between seven (7) and eight (8) percent Once the FLEV is calculated, an additional calculation based on the specific light delivery system may be made. The delivery system calculation determines what irradiation time period is needed to deliver the FLEV to the fluid, taking into consideration a variety of factors related to the light source and its present ability to deliver light. This calculation may preferably take into consideration factors such as the shape of the light source, the lamp decay over time, the size of the light beam, and the volume of the fluid being irradiated.

The variable L (mW/cm²) accounts for decay of the output of the light source over time and depends upon the properties of the lamp source used, preferably measured at a fixed position from the lamp center line. By way of example, L may be determined by taking hourly measurements of an exemplary lamp over the lamp's lifetime. As time progresses, the lamp intensity decreases. In a specific embodiment, once the hourly measurements are plotted, an equation can be created to match the measurements. Then, the equation can be utilized to determine the value of L by merely knowing how many lamp hours have been used. In an alternate embodiment, a database containing the lamp life measurements can be directly accessed.

For example, in a particular embodiment of the present invention, FIG. 11 represents, in a prototype look-up table, the L value (mW/cm²) over 150 hourly measurements for a lamp utilized in the UVAR® system taken 25 cm from its center. These measurements result in the following single lamp irradiance decay equation:

$$L = a + b^*(x)^{0.5}*\ln(x) + c^*\ln(x) \qquad (3.5)$$

The L value allows one to adjust for lamp life in determining the length of time the light source irradiates the targets to achieve the desired result. Based on the L values of FIG. 11, an exemplary single lamp irradiance decay equation is determined where a equals 0.78552878, b equals −0.00059106023, and c equals −0.032384473. This equation, as well as the table for L values for the light source utilized, may be stored and accessible for example, in system memory or in a look-up table.

In the exemplary UVAR® system, the photoactivation chamber is located between two banks of UVA lamps and the buffy coat suspension is recirculated through a serpentine path inside the photoactivation chamber. The blood film thickness in the chamber is the same, about 1.4 mm thick. At this blood film thickness, with hematocrit value at least around few percent, the irradiating UVA light is completely absorbed by the blood film and the total amount of UVA energy delivered to the each ml of circulating buffy coat suspension can be calculated. This value is 255 Joules/ml in the UVAR® system.

The irradiance of UVA light reaching the surface of the target cells in the suspension is attenuated by the red blood cells in the light path. The red blood cell is almost completely opaque to the UVA light. Under these conditions, it is reasonable to assume that the attenuation of the irradiance is inversely proportional to the red blood cell concentration in the light path. The concentration of white blood cells is about one order of magnitude less than that of red blood cells and also the white blood cell is much less opaque to UVA light than red blood cells. Therefore, the amount of attenuation caused by the white blood cells will be insignificant and may be ignored in the derivation of irradiation time equation.

The total amount of UVA energy delivered to the each ml of the circulating buffy coat suspension can be expressed as:

$$Ev = k*H \tag{3.6}$$

where Ev=Total amount of UVA energy delivered per unit volume, Joules/ml k=Proportional constant H=Hematocrit.

In the UVAR® system, the value of Ev is 255 Joules/ml and the average hematocrit value is about 3.5%. Therefore, k=255/3.5.

UVA energy is delivered through the irradiation chamber and to the surface of the buffy coat suspension film inside the irradiation chamber while the buffy coat film is flowing inside the irradiation chamber. The total amount of UVA energy delivered to the total volume of the buffy coat suspension can be calculated by multiplying the irradiance at blood film surface (through the chamber wall), the irradiation period and the irradiated blood film area. Also, the UVA energy delivered to a unit volume, Ev, can be expressed by dividing the total amount of UVA energy delivered divided by the total buffy coat suspension volume.

$$Ev = \frac{(Io*1000*A*t*60)}{V} \tag{3.7}$$

where Ev=UVA energy delivered per unit volume, J/ml

Io=UVA irradiance at blood film surface, $mW/cm^2$

A=Area of blood film irradiated inside irradiation chamber, $1330 \, cm^2$ t=Irradiation period, minutes V=Total buffy coat suspension volume in the circulation loop, ml.

The multiplication factors, 1000 and 60, may be utilized for unit correction from milliwatts to watts and from minutes to seconds.

Combining equations 3.6 and 3.7, and substituting k=255/3.5 and A=1330 $cm^2$, the irradiation period can be expressed as:

$$t_{sec} = 0.9128*60*H*(V/A)/Io \tag{3.8}$$

The equation for the average irradiance value, Io, of the UVA light at blood film surface inside the irradiation chamber can be derived as follows.

The UVA light reaching the surface of the blood film inside the UVAR® irradiation chamber comes from a light set consisting of nine (9) lamps. In the instrument light box, the UVA light passes through UVA transparent glass and the acrylic irradiation chamber wall before it reaches the blood film. Also, the UVA output is not uniform along the length of the tubular fluorescence UVA lamp. The output is higher in the middle section of the lamp and lower near the ends of the lamp. Therefore, the average irradiance value of the UVA light reaching the blood film can be obtained by measuring the irradiance at points along the light set and calculating their average value. However, since lamp output decays over time, it is extremely difficult to measure all points simultaneously at a given lamp time. As described below, this problem was resolved by the relationship of this average value to the average single lamp irradiance value at one fixed point that can be measured quickly.

Figure 12:
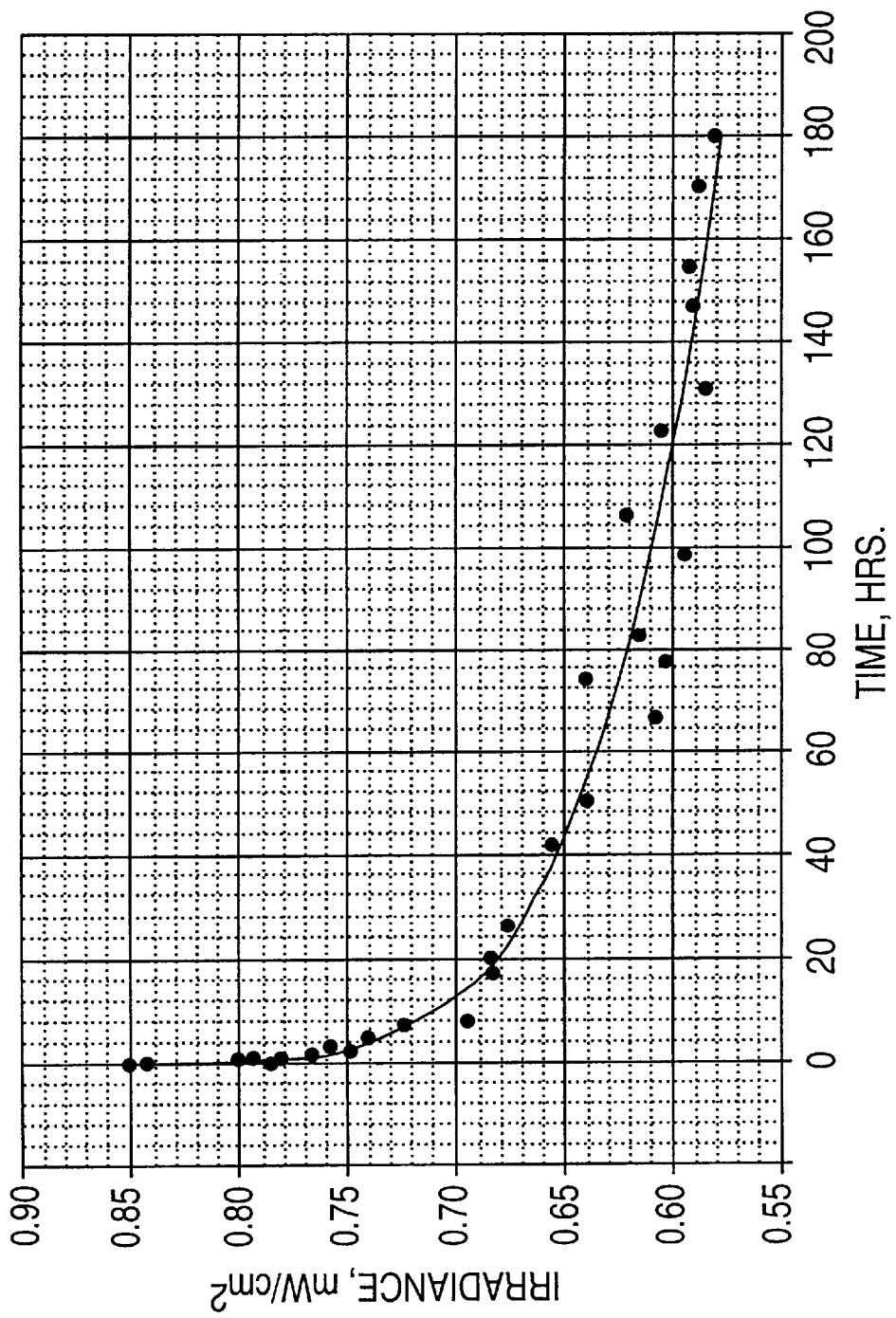
FIG. 12 is a graph of average single lamp irradiance measured at a distance of 25 cm from the center line of a lamp over time.

FIG. 12 shows the average UVA irradiance value of six (6) single lamps measured at mid-point and at a 25 cm distance from the lamp center line as a function of lamp life. The irradiance value decays very rapidly at the beginning and decreases more gradually as the lamp life increases. After around 60 hours of use, the lamp output decays rather slowly and it allows enough time to measure points in the light set and calculate the average irradiance value. The irradiance measurements were made at the 61.5 hour point and the 150 hour point in several light sets. The values were 15.11 and 11.19 $mW/cm^2$ at 61.5 hours and 150 hours, respectively. The ratios of these average irradiance values in the light box and the average single lamp irradiances at corresponding lamp life were calculated. The ratios were 23.9 at the 61.5 hour point and 21.9 at the 150 hour point, resulting in the average value of 22.9.

Io in Equation 3.8 can be expressed as:

$$Io = k*L*[T/100] \tag{3.9}$$

where k=Irradiance ratio of the light box and single lamp, 22.9

L=Single lamp irradiance, $mW/cm^2$

T=Percent UVA transmittance of acrylic irradiation chamber, 92%.

Substituting equation 3.9 for Io in equation 3.8 and actual values for corresponding variables, the irradiation time equation 3.8 becomes:

$$t = (2.59958*V*H)/L \tag{4.0}$$

where L is the single lamp irradiance expressed as a regression line equation based on measured data points shown in FIGS. 11 and 12.

In an exemplary UVAR® system used in CTCL ECP applications, the following equation 4.1 is used via the methods and systems of the present invention to determine irradiation times:

$$t_{min} = \frac{(91.28 * V * H)}{(T * k * L_1)} \quad (4.1)$$

where $t_{min}$=Irradiation time, minutes
V=Volume of the fluid in the treatment/recirculation loop, ml
H=Hematocrit
T=92 (% transmittance of irradiation chamber)
k=23.9 (a constant based on a ratio of the intensity of one lamp measured at one point in the fluid to the intensity of the entire lamp set in the UVAR® system).
Correcting for time in seconds, gives:

$$t_{sec} = \frac{(60 * 91.28 * V * H)}{(T * k * L_1)} \quad (4.2)$$

Inserting constants gives:

$$t_{sec} = \frac{(60 * 91.28 * V * H)}{(92 * 23.9 * L_1)} \quad (4.3)$$

Collecting constants gives:

$$t_{sec} = \frac{(2.49081 * V * H)}{L_1} \quad (4.4)$$

Referring to FIG. 11, and using the following parameters:
lamp age=2.7 hours
V=210 ml
H=2.9
The L value at lamp life of 2 hours is 7625 in FIG. 11. The L value at lamp life of 3 hours is 7488. Linear interpolation using integer arithmetic gives:

$$7625 + \left(\frac{(7488 - 7625) * 7}{10}\right) = 7625 + -95 = 7530 \quad (4.5)$$

Therefore:

$$t_{sec} = \frac{(2491 * 210 * 29)}{7530} = 2014 \text{ sec.} = 33.57 \text{ min} \quad (4.6)$$

The UVAR® instrument, in a specific embodiment, uses two lamp banks. The lamp ages of these banks can differ, and theoretically, so can their irradiation time tables. To account for this, the complete calculation is preferably run twice, once for each lamp bank, and the values may be averaged. This value is the photoactivation time. Once the calculation is run the time remaining is preferably immediately decremented by the amount of time the UV lamps have already been on in the UVAR® system.

Once the irradiation time period is calculated, the present invention contemplates the additional step of delivering the light energy, for that period of time, to the fluid containing targets. In a particular embodiment of the present invention, the system then may instruct the photoactivation device to deliver the FLEV to the fluid for the determined irradiation period. This may be accomplished via computer or any other known methods. Indeed, the methods and systems of the present invention contemplate the predetermination of any of the variables such as TELEV, FLEV, thickness ratio, irradiation period, uniform fluid thickness, non-target thickness, and/or hematocrit value in the buffy coat. Any or all of these predetermined variables may be accessible by the user, e.g., available in tabular form, and, in a particular embodiment of the present invention, stored or accessible in computer memory.

In order to assess the accuracy of the calculated amount of UVA energy predicted by equations 2.0 and 2.4, an equal number of lymphocytes were suspended in clear phosphate buffered saline and in a buffy coat suspension with 3.5% hematocrit. These two suspensions were exposed to a UVA light in the presence of 100 ng/ml of 8-MOP. Controls were also provided in which no 8-MOP was added to the suspensions. The degree of the injury to the cells by this treatment at the same 8-MOP concentration is dependent on the UVA energy dosage and can be measured by the cell viability.

The irradiation periods were calculated by equations 2.0 and 2.4 to deliver approximately 1.4 Joule/cm$^2$ of UVA energy to the lymphocytes in the fluids. Since the phosphate buffered saline is transparent to UVA light, the irradiation period was calculated based on the incident irradiance (equation 2.0). The irradiation period for the lymphocytes in the buffy coat suspension was calculated by equations 2.0 and 2.4. The post-irradiation cell viability of both samples was measured to compare the injury to the cells. The cell viability of both samples were around 19% or less seven days after the irradiation while that of the untreated control sample was around 85% or higher. This result shows that the lymphocytes in the phosphate buffered saline and the buffy coat suspension received the same amount of injury and resultant cell death. Indeed, the lymphocytes in both samples received the same amount of UVA energy as calculated by each equation.

Equation 2.0 may preferably be used with any partially transparent solutions or suspensions. It requires an accurate transmittance (T) measurement of a known thickness (D) of the fluid, preferably under conditions where the materials in the fluid are homogeneous. Equation 2.4, may be particularly applicable with fluids comprising red blood cells.

Referring to the associated Figures, in a specific embodiment of the invention, FIG. 1 depicts a extracorporeal photopheresis system 100 as an application of phototherapy according to the present invention as applied to the treatment of leukocytes. See PCT Application WO 97/36581. The phototherapy system 100 includes a photoactivatable drug, 8-MOP 110, a patient 120, a biological fluid extraction device 130 for extracting blood, a centrifuge device 140 to separate out the buffy coat from the blood, a photoactivation device 150, a fluid (i.e., buffy coat) insertion device 160, and a blood insertion device 170. One skilled in the art will appreciate that system 100 may contain additional or different devices and can support a variety of phototherapy applications, as mentioned above. See U.S. Pat. Nos. 4,921,473, 4,838,852, 5,147,289, 5,150,705, 5,383,847, 5,433,738, and 5,459,322, each of which are expressly incorporated by reference herein and relate to various applications to which the systems and apparatus of the present invention can be utilized.

FIGS. 2A and 2B depict a flow diagram 200 of the blood in the photopheresis system in FIG. 1. The first step is to mix the patient's 120 blood with 8-MOP 110 (step 202). In the present embodiment, the patient 120 is orally administered the 8-MOP 110 and, over the course of a few hours, the drug mixes with the patient's 120 blood. Next, after the drug 110 sufficiently interacts with the blood (step 204) an amount of blood-drug mixture is extracted 130 (step 206) and transferred to a separator, such as a centrifuge device 140 (step 208).

After the blood-drug mixture is transferred to the centrifuge device 140, the centrifuge device 140 separates the mixture (step 210). A particular centrifuge device uses an optical sensor to determine when to separate (or skim) the fluid. First, the centrifuge skims off the plasma, then the buffy coat, which contains the target material (i.e., 8-MOP in the leukocytes), and then the red blood cells. The centrifuge device uses an optic sensor located inside the centrifuge chamber that measures deflected light. This optic sensor, by measuring the deflected light in the centrifuge determines when to skim off the separated fluids or material. After separation, the buffy coat and a percentage of plasma are re-combined. The plasma is the medium in which the leukocytes and 8-MOP reside. Even after separation, however, the separated buffy coat and plasma mixture may comprise some red blood cells and platelets, since the separation process may not be able to achieve complete separation. These remaining red blood cells and platelets, contained in the buffy coat, are the non-target attenuators of light. In the present embodiment, the red blood cells are the dominant non-targets since they are the major attenuators of light, when compared to other attenuating material in the target fluid.

Once the target fluid (i.e., the buffy coat mixture) is separated, a second optic sensor determines whether the target fluid contains a desired hematocrit (percentage of red blood cells) (step 212). In a particular embodiment, a desired hematocrit is about one (1) to two (2) percent. This second optic sensor, which measures transmittance, determines whether a desired hematocrit is reached (i.e., 1% in the present embodiment). If the hematocrit percentage is not at the desired percentage, then additional blood-drug mixture is processed by the centrifuge (step 210).

If the non-target fluid contains the desired hematocrit percentage, then the centrifuge determines what separated fluid it is processing (step 214). If the centrifuge is processing the non-target fluid, then the centrifuge combines the remaining separated plasma with the separated red blood cells and transfers the mixture to the separated blood insertion device 170 (step 216). Then, the blood insertion device returns the red blood cell/plasma mixture to the patient (step 218) and processing stops.

Figure 3:
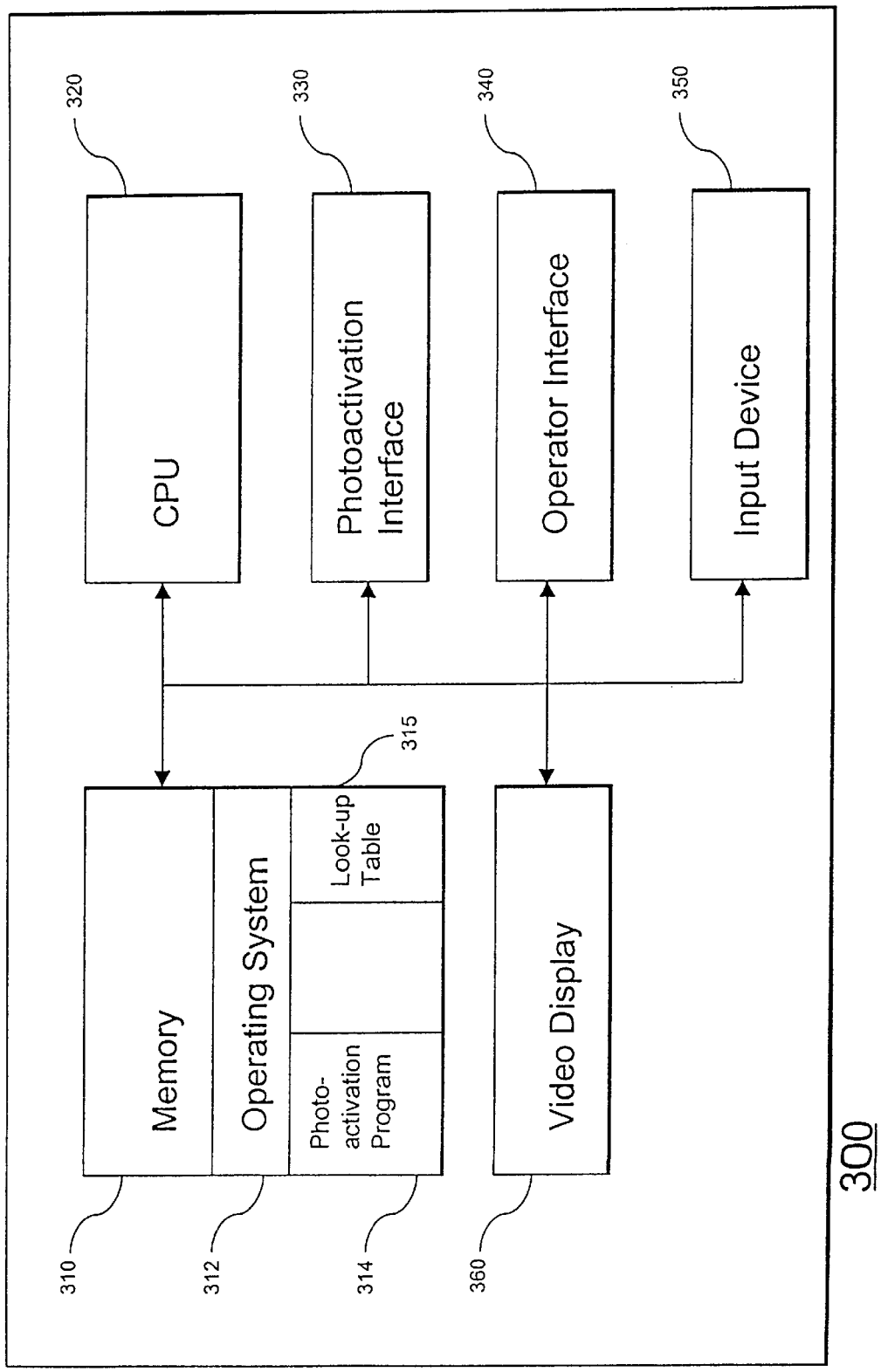
FIG. 3 is a diagram 300 of a computer system for controlling the photoactivation device according to an implementation of the present invention.

If the centrifuge is processing the target fluid, the centrifuge then transfers the target fluid to the photoactivation device (step 220). Step 220 and step 216 may happen concurrently. The photoactivation chamber 150 then irradiates the fluid for a period of time (step 222). Computer 300 controls the photoactivation chamber 150 as illustrated in FIG. 3 and described in the corresponding discussion. The target fluid, now treated, is then transferred to a fluid insertion device 160 (step 224). Then, the target insertion device returns the red blood cell/plasma mixture to the patient (step 226) and processing stops. FIG. 3 is a diagram of a computer 300 for controlling the photoactivation device 150 according to the implementation of the present invention. The computer 300 includes a memory 310, a central processing unit (CPU) 320, a photoactivation interface 330, an operator interface 340, an input device 350, and a video display 360. One skilled in the art will appreciate that computer 300 may contain additional or different components. The memory 310 further includes an operating system 312, a photoactivation program 314, and look-up table 315. The look-up table 315 may comprise a storage location in the memory 310 and may contain tables that correspond to data needed by the photoactivation program 314. The individual tables and the corresponding data are described in further detail in the descriptions that correspond to FIGS. 4 through 9. The photoactivation program 312 acquires the FLEV. The FLEV could be obtained by accessing the look-up table 315, via the input device 350, or by calculation as further described in the descriptions that correspond to FIGS. 4 through 9.

Although aspects of the present invention are described as being stored in memory 310, one skilled in the art will appreciate that one or more of these aspects may also be stored in other computer-readable media, such as secondary storage devices, like hard disks, floppy disks, or CD-ROMs; a carrier wave from the Internet; or other forms of RAM or ROM. Indeed, each of the methods, or particular steps contained therein, may be performed by or stored in a computer or computer readable media.

FIG. 4 depicts a flowchart 400 of the steps performed by the photoactivation program 314 when requested to determine and then deliver an amount of light energy to a fluid containing targets whereby the targets in the fluid will receive an effective amount of light energy. The first step performed by the photoactivation program 314 is to obtain the TELEV (step 402). The desired result is previously defined and is based on the phototherapy application. For instance, when photopheresis is used to treat CTCL, the TELEV applied to the leukocytes preferably causes at least fifty (50) percent of the leukocytes to gradually die within six (6) days after exposure to the light energy.

The TELEV may be obtained by accessing, for example, a look-up table 315 that contains TELEV data. In an alternative embodiment of the present invention, the photoactivation program 314 may obtain the TELEV via the input device 350. FIG. 5 illustrates how the TELEV may be clinically identified once the desired result is known.

Once the TELEV is obtained, the next step is to obtain the average light energy factor for the fluid (step 404). The ALE factor is the percent of incident light energy that will be delivered to an average unit area of fluid. The ALE factor may be obtained by accessing the portion of the look-up table 315 that pertains to ALE factor data. In an alternative embodiment of the present invention, the ALE factor may be obtained via the input device 350.

In an alternative embodiment of the present invention, the ALE factor may be obtained for any target in a biological fluid from knowing the average light energy value (Joules/$cm^2$) at the unit surface area of the targets in the fluid and knowing the light energy value (Joules/$cm^2$) at the incident surface of the biological fluid. The description that accompanies FIG. 6 illustrates such a procedure for obtaining the ALE factor.

In an alternative embodiment of the present invention, the ALE factor may be obtained from knowing the fluid's thickness ratio and the light transmittance value of a known fluid thickness. The thickness ratio is the ratio of the uniform thickness of the fluid and the average thickness of the non-target in the fluid. The non-target is material in the fluid that attenuates light energy. The description that accompanies FIG. 7 illustrates such a procedure for obtaining the ALE factor.

In an alternative embodiment of the present invention, when fluid comprises red blood cells as non-targets that attenuate light energy, the ALE factor may be obtained from knowing the thickness ratio and knowing the percentage of hematocrit or red blood cells in the fluid. The description that accompanies FIG. 8 illustrates such a procedure for obtaining the ALE factor.

In an alternative embodiment of the present invention, when fluid comprises red blood cells as non-targets that attenuate light energy, the ALE factor may be obtained from knowing the uniform thickness of the fluid and knowing the percentage of hematocrit or red blood cells in the fluid. The description that accompanies FIG. 9 illustrates such a procedure for obtaining the ALE factor.

After obtaining the ALE factor, the next step is to obtain the FLEV or the amount of light energy needed to be delivered to the fluid so that the targets in the fluid will receive the TELEV (step 406). In a preferred embodiment, the FLEV can be calculated by knowing the TELEV and the ALE factor and using equation 1.0, as described previously.

After obtaining the FLEV, one may then obtain the irradiation time period (step 408). The irradiation time period is the amount of time needed for the lamp or light energy source to deliver the FLEV to the fluid. The irradiation time period is obtained by accessing the portion of the look-up table 315 that pertains to irradiation time period data.

In an alternative embodiment of the present invention, the irradiation time period can be calculated. Factors that might be considered in irradiation time period calculation are lamp decay or power, the shape of the lamp, or the volume of fluid to be irradiated. In an alternative embodiment of the present invention, when the fluid comprises non-target red blood cells, the irradiation time period can be calculated knowing the fluid's volume, the percent of red-blood cells in the fluid, and the decay life of the light source using, for example, an equation such as equation 1.5, as described previously.

After obtaining the irradiation time period, one may then instruct the photoactivation device 150 to engage the light energy lamp for the irradiation time period.

FIG. 5 depicts a flowchart 500 of the steps performed when clinically obtaining the TELEV. The first step in clinically obtaining the TELEV is to obtain the desired result of the phototherapy (step 502). The next step is to place sample targets in a non-attenuating fluid, which is often a biological or chemical fluid (step 504). One skilled in the art will recognize that there are numerous non-fluid mediums and other fluid types that can support targets such as saline, and filtered plasma. In an alternative embodiment, when targets initially reside in a fluid, samples of the fluid can be used for the clinical tests, provided any or most of the non-attenuation materials are filtered out.

Next, samples of the fluid containing the targets are irradiated with varying amounts of light energy (step 506). After irradiating the sample fluids, a TELEV is identified that corresponds to the sample that produced the desired the result (step 508). One skilled in the art will appreciate that any TELEV is specific to the particular application of the methods and systems of the present invention.

FIG. 6 depicts a flowchart 600 of the steps performed by the photoactivation program 314 when obtaining the ALE factor. This procedure for obtaining the ALE factor may be used for any fluid containing targets. The first step to obtain the ALE factor is to obtain the average light energy value at the unit surface area of the targets in the fluid (step 602). The average light energy value at the unit surface area can be obtained by accessing the portion of the look-up table 315 that pertains to average light energy value at the unit surface area data. In an alternative embodiment of the present invention, the photoactivation program 314 may obtain the average light energy value at the unit surface area via the input device 350.

The next step is to obtain the light energy value at the incident surface of the biological fluid (step 604). The light energy value at the incident surface can be obtained by accessing the portion of the look-up table 315 that pertains to light energy value at the incident surface data. In an alternative embodiment of the present invention, the photoactivation program 314 may obtain the light energy value at the incident surface via the input device 350. The ALE factor may then be calculated using equation 1.0 (step 606).

FIG. 7 depicts a flowchart 700 of the steps performed by the photoactivation program 314 when obtaining the ALE factor. This procedure for obtaining the ALE factor may be used for any biological fluid containing targets. However, the accuracy of this equation is maximized when a homogeneous mixture of targets and non-targets in the fluid is provided. In a particular embodiment of the present invention, a homogeneous biological fluid mixture may be obtained by stirring the biological fluid containing the targets and non-targets.

To obtain the ALE factor, one first obtains the thickness ratio of the fluid (step 702). The thickness ratio is the ratio of the uniform thickness of the fluid and the average thickness of the non-target in the fluid. The thickness ratio, the uniform fluid thickness, and the non-target's thickness can be obtained by obtaining these values by, for example, accessing a look-up table 315 that contains data relating to these parameters. In an alternative embodiment of the present invention, the photoactivation program 314 may obtain the thickness ratio, the uniform fluid thickness, and the non-target thickness via the input device 350. Once the uniform fluid thickness and the non-target thickness data are obtained, the thickness ratio can be calculated by dividing the uniform fluid thickness by the non-target thickness.

After obtaining the thickness ratio, one then may obtain a light transmittance value of a known fluid thickness (step 704). The irradiation period can be obtained by accessing the portion of a look-up table 315 that pertains to light transmittance value of a known fluid thickness data. In an alternative embodiment of the present invention, the photoactivation program 314 may obtain a light transmittance value of a known fluid thickness. The ALE factor may then be calculated using equation 1.1 (step 706).

FIG. 8 depicts a flowchart 800 of the steps performed by the photoactivation program 314 when obtaining the ALE factor. This procedure for obtaining the ALE factor may be used for biological fluid that comprises red blood cells as non-targets that attenuate light energy. The accuracy of this equation may depend on how well the fluid is stirred. The first step to obtain the ALE factor is to obtain the thickness ratio (step 802). The thickness ratio is the ratio of the uniform thickness of the fluid and the average thickness of the non-target in the fluid. The non-target is the material in the fluid that attenuates light energy. The thickness ratio, the uniform fluid thickness, and the non-target's thickness can be obtained by accessing the portion of the look-up table 315 that pertains to thickness ratio, the uniform fluid thickness, and the non-target thickness data, respectively. In an alternative embodiment of the present invention, the photoactivation program 314 may obtain the thickness ratio, the uniform fluid thickness, and the non-target's thickness via the input device 350. Once obtaining the uniform fluid thickness and the non-target thickness data, the thickness ratio can be calculated by dividing the uniform fluid thickness by the non-target thickness.

After obtaining the thickness ratio, the next step is to obtain percentage of red blood cells or hematocrit per unit of biological fluid (step 804). The red-blood cell percentage can be obtained by reading, for example, the optical or electromagnetic profile of the fluid by known means or by accessing the portion of the look-up table 315 that pertains to red-blood cell percentage data. In an alternative embodiment of the present invention, the photoactivation program 314 may obtain the red-blood cell percentage via the input device 350. The ALE factor may then be calculated using equation 1.2 (step 806).

FIG. 9 depicts a flowchart 900 of the steps performed by the photoactivation program 314 when obtaining the ALE factor. This procedure for obtaining the ALE factor may be used for biological fluid that comprises red blood cells as non-targets that attenuate light energy and have a stacking factor of between 1 and 2. The accuracy of the results of this equation may depend on how well the fluid is stirred. The first step to obtain the ALE factor is to obtain the uniform fluid thickness (step 802). The uniform fluid thickness can be obtained by accessing the portion of the look-up table 315 that pertains to uniform fluid thickness data. In an alternative embodiment of the present invention, the photoactivation program 314 may obtain the uniform fluid thickness via the input device 350.

After obtaining the uniform fluid thickness, the next step is to obtain the percentage of red blood cells or hematocrit per unit of biological fluid (step 904). The red blood cell percentage can be obtained by reading, for example, the optical or electromagnetic profile of the fluid by known means or by accessing the portion of the look-up table 315 that pertains to red blood cell percentage data. In an alternative embodiment of the present invention, the photoactivation program 314 may obtain the red blood cell percentage via the input device 350. The ALE factor may then be calculated using equation 1.3 (step 906).

FIG. 10 depicts a graph of ALE factors calculated for a fluid comprising red blood cells as non-targets for three different fluid thicknesses (1 mm, 2 mm, and 3 mm). These ALE factors were calculated using equations 1.1 (Analytical Model) and 1.3 (Stacking Model). The ratio of the average light energy delivered to the targets in the fluid and the light energy delivered to the incident point is plotted as a function of percent hematocrit at different fluid thickness.

The present invention is not to be limited in scope by the specific embodiments described which are intended as single illustrations of individual aspects of the invention and functionally equivalent methods and components are within the scope of the invention, in addition to those shown and described herein will become apparent to those skilled in the art from the foregoing description and accompanying drawings. Such modifications are intended to fall within the scope of the appended claims.

I claim:

1. A method of determining a fluid light energy value for delivery to a biological fluid comprising targets and non-target material, wherein an effective amount of light energy is desired to be delivered to said targets and wherein said non-target material attenuates said light energy destined for said targets, comprising the steps of:

obtaining said target's effective light energy value;

obtaining said fluid's average light energy factor; and calculating said fluid light energy value for delivery to said biological fluid, wherein determining the fluid light energy value is performed by one or more computer processors.

2. The method of claim 1 further comprising the step of:

delivering the fluid light energy value to said biological fluid.

3. The method of claim 1, wherein determining the fluid's light energy value is performed by one or more computer processors.

4. The method of claim 1 further comprising the step of:

providing a homogenous biological fluid mixture.

5. The method of claim 1, wherein said non-target material comprises red blood cells.

6. The method of claim 5, wherein obtaining said average light energy factor comprises the steps of:

obtaining a thickness ratio;

obtaining a red blood cell percentage for said biological fluid; and calculating the average light energy factor for said targets in said biological fluid.

7. The method of claim 6, wherein obtaining said average light energy factor is performed by one or more computer processors.

8. The method of claim 6, wherein obtaining said thickness ratio comprises the step of:

accessing a thickness ratio table.

9. The method of claim 6, wherein obtaining said red blood cell percentage comprises the step of:

accessing a red blood cell percentage table.

10. The method of claim 6 further comprising the step of:

providing a homogenous biological fluid mixture.

11. The method of claim 6, wherein said biological fluid comprises leukocyte-rich buffy coat.

12. The method of claim 11, wherein said biological fluid is treated with a light energy activatable drug.

13. The method of claim 12, wherein said drug comprises 8-methoxypsoralen.

14. The method of claim 13, wherein said light energy comprises ultraviolet light energy.

15. The method of claim 14, wherein said ultraviolet light energy comprises ultraviolet A light energy.

16. The method of claim 15, wherein determining the fluid light energy value is performed by one or more computer processors.

17. The method of claim 13, wherein obtaining said red blood cell percentage comprises the step of:

accessing a red blood cell percentage table.

18. The method of claim 6, wherein obtaining said thickness ratio comprises the steps of:

obtaining a uniform thickness for said biological fluid;

obtaining a thickness for said non-target; and calculating the thickness ratio.

19. The method of claim 18, wherein obtaining said thickness ratio is performed by one or more computer processors.

20. The method of claim 18, wherein obtaining said uniform film thickness comprises the step of:

accessing an uniform thickness ratio table.

21. The method of claim 18, wherein obtaining said thickness for said non-target comprises the step of:

accessing a non-target thickness table.

22. The method of claim 5, wherein obtaining said average light energy factor comprises the steps of:

obtaining a uniform thickness for said biological fluid;

obtaining a red blood cell percentage for said biological fluid; and calculating the average light energy factor for said targets in said biological fluid.

23. The method of claim 22, wherein theoretical stacking of said red-blood cells does not occur.

24. The method of claim 22, wherein said biological fluid comprises up to about twenty percent said red blood cells.

25. The method of claim 22 further comprising the step of:

obtaining a stacking factor.

26. The method of claim 22, wherein said stacking factor is between 1 and 2.

27. The method of claim 26, wherein said stacking factor is 1.5.

28. The method of claim 22, wherein obtaining said average light energy factor is performed by one or more computer processors.

29. The method of claim 22, wherein obtaining said uniform thickness comprises the step of:
accessing a biological fluid thickness table.

30. The method of claim 22 further comprising the step of:
providing a homogenous biological fluid mixture.

31. The method of claim 22, wherein said biological fluid comprises leukocyte-rich buffy coat.

32. The method of claim 31, wherein said biological fluid is treated with a light energy activatable drug.

33. The method of claim 32, wherein said drug comprises 8-methoxypsoralen.

34. The method of claim 33, wherein said light energy comprises ultraviolet light energy.

35. The method of claim 34, when said ultraviolet light energy comprises ultraviolet A light energy.

36. The method of claim 35, wherein determining said fluid light energy value is performed by one or more computer processors.

37. The method of claim 1, wherein said biological fluid comprises leukocyte-rich buffy coat.

38. The method of claim 37, wherein said biological fluid is treated with a light energy activatable drug.

39. The method of claim 38, wherein said drug comprises 8-methoxypsoralen.

40. The method of claim 39, wherein said light energy comprises ultraviolet light energy.

41. The method of claim 40, wherein said ultraviolet light energy comprises ultraviolet A light energy.

42. The method of claim 41, wherein determining said fluid light energy value is performed by one or more computer processors.

43. The method of claim 1, wherein said calculating step comprises:
calculating an irradiation time period required by a light energy source to deliver said fluid's light energy value.

44. The method of claim 43 further comprising the step of:
delivering the fluid's light energy value to said biological fluid.

45. The method of claim 43, wherein calculating the irradiation time period is performed by one or more computer processors.

46. The method of claim 43, wherein calculating the irradiation time period comprises:
obtaining a decay life value for said light energy source.

47. The method of claim 43, wherein said non-target material comprises red blood cells, and wherein calculating the irradiation time period comprises:
obtaining a volume of biological fluid value;
obtaining a percent of red blood cells value; and
obtaining a decay life value for said light energy source.

48. The method of claim 1, wherein obtaining said targets' effective light energy value comprises the step of:
accessing a targets' effective light energy value table.

49. The method of claim 48, wherein obtaining said target's effective light energy value is performed by one or more computer processors.

50. The method of claim 1, wherein obtaining said target's effective light energy value comprises the steps of:
placing said targets in fluid, wherein said targets in said fluid do not receive attenuated light energy; and
irradiating said fluid with sample light energy values.

51. The method of claim 50, wherein said fluid comprises saline.

52. The method of claim 50, wherein said fluid comprises plasma.

53. The method of claim 1, wherein obtaining said target's effective light energy value comprises the steps of:
placing said leukocytes in fluid comprising saline; and
identifying a light energy value whereby a desired percentage of said leukocytes will die over the course of a specified time after exposure to said light energy.

54. The method of claim 1, wherein obtaining said target's effective light energy value comprises the steps of:
obtaining sample biological fluids from donors;
irradiating said targets in said biological fluids with sample light energy values; and
determining the target's effective light energy value.

55. The method of claim 1, wherein obtaining said average light energy factor comprises the step of:
accessing a light energy factor table.

56. The method of claim 55, wherein obtaining said average light energy factor is performed by one or more computer processors.

57. The method of claim 1, wherein the obtaining said average light energy factor comprises the steps of:
obtaining an average light energy value at a unit surface area of the targets in the biological fluid;
obtaining a light energy value at an incident surface of the biological fluid film; and
calculating the average light energy factor for said targets in said biological fluid.

58. The method of claim 57, wherein obtaining said average light energy factor is performed by one or more computer processors.

59. The method of claim 57, wherein obtaining said average light energy value at a unit surface area comprises the step of:
accessing an average light energy value at a unit surface area table.

60. The method of claim 57, wherein obtaining said light energy value at an incident surface comprises the step of:
accessing a light energy value at an incident surface table.

61. The method of claim 57 further comprising the step of:
providing a homogenous biological fluid mixture.

62. The method of claim 28, wherein said non-target material comprises red blood cells.

63. The method of claim 57, wherein said biological fluid comprises leukocyte-rich buffy coat.

64. The method of claim 63, wherein said biological fluid is treated with a light energy activatable drug.

65. The method of claim 64, wherein said drug comprises 8-methoxypsoralen.

66. The method of claim 65, wherein said light energy comprises ultraviolet light energy.

67. The method of claim 66, wherein said ultraviolet light energy comprises ultraviolet A light energy.

68. The method of claim 67, wherein determining said fluid light energy value is performed by one or more computer processors.

69. The method of claim 1, wherein obtaining said average light energy factor comprises the steps of:
obtaining a thickness ratio;
obtaining a light transmittance value of a known fluid film thickness; and
calculating the average light energy factor for said targets in said biological fluid.

70. The method of claim 69, wherein obtaining said average light energy factor is performed by one or more computer processors.

71. The method of claim 69, wherein obtaining said thickness ratio comprises the step of:

accessing a thickness ratio table.

72. The method of claim 69, wherein obtaining said irradiation period comprises the step of:

accessing a irradiation period table.

73. The method of claim 69 further comprising the step of:

providing a homogenous biological fluid mixture.

74. The method of claim 69, wherein said non-target material comprises red blood cells.

75. The method of claim 42, wherein obtaining said thickness ratio comprises the steps of:

obtaining a uniform thickness for said biological fluid;

obtaining a thickness for said non-target; and calculating the thickness ratio.

76. The method of claim 75, wherein obtaining said uniform film thickness comprises the step of:

accessing a uniform thickness table.

77. The method of claim 75, wherein obtaining said non-target thickness comprises the step of:

accessing a non-target thickness table.

78. The method of claim 75, wherein said non-targets comprise red blood cells.

79. The method of claim 78, wherein obtaining said thickness ratio is performed by one or more computer processors.

80. The method of claim 69, wherein said biological fluid comprises leukocyte-rich buffy coat.

81. The method of claim 80, wherein said biological fluid is treated with a light energy activatable drug.

82. The method of claim 81, wherein said drug comprises 8-methoxypsoralen.

83. The method of claim 82, wherein said light energy comprises ultraviolet light energy.

84. The method of claim 83, wherein said ultraviolet light energy comprises ultraviolet A light energy.

85. The method of claim 84, wherein determining the desired amount of said ultraviolet light energy is performed by one or more computer processors.

86. A computer system for determining a fluid light energy value for delivery to a biological fluid comprising targets and non-target material, wherein an effective amount of light energy is desired to be delivered to said targets and wherein said non-target material attenuates said light energy destined for said targets, comprising:

a computer processor;

a memory which is operatively coupled to the computer processor; and a computer process stored in said memory which executes in the computer processor and which includes:

an obtainer configured to obtain said target's effective light energy value;

an obtainer configured to obtain said fluid's average light energy factor; and a calculator configured to calculate said fluid's light energy value for delivery to said biological fluid.

87. The computer system of claim 86, wherein said non-target material comprises red blood cells.

88. The computer system of claim 87, wherein said obtainer configured to obtain the average light energy factor comprises the steps of:

an obtainer configured to obtain a uniform thickness for said biological fluid;

an obtainer configured to obtain a red blood cell percentage for said biological fluid; and a calculator configured to calculate the average light energy factor for said targets in said biological fluid.

89. The computer system of claim 88, wherein theoretical stacking of said red-blood cells does not occur.

90. The computer system of claim 88, wherein said biological fluid comprises up to about twenty percent said red blood cells.

91. The computer system of claim 88 further includes:

an obtainer configured to obtain said stacking factor.

92. The computer system of claim 88, wherein said stacking factor is between 1 and 2.

93. The computer system of claim 92, wherein said stacking factor is 1.5.

94. The computer system of claim 88, wherein said obtainer configured to obtain said uniform thickness includes:

an accessor configured to access a biological fluid thickness table.

95. The computer system of claim 88, wherein said obtainer configured to obtain said red blood cell percentage includes:

an accessor configured to access a red blood cell percentage table.

96. The computer system of claim 88, wherein said biological fluid comprises leukocyte-rich buffy coat.

97. The computer system of claim 96, wherein said biological fluid is treated with a light energy activatable drug.

98. The computer system of claim 97, wherein said drug comprises 8-methoxypsoralen.

99. The computer system of claim 98, wherein said light energy comprises ultraviolet light energy.

100. The computer system of claim 99, wherein said ultraviolet light energy comprises ultraviolet A light energy.

101. The computer system of claim 86, wherein said biological fluid comprises leukocyte-rich buffy coat.

102. The computer system of claim 101, wherein said biological fluid is treated with a light energy activatable drug.

103. The computer system of claim 102, wherein said drug comprises 8-methoxypsoralen.

104. The computer system of claim 103, wherein said light energy comprises ultraviolet light energy.

105. The computer system of claim 104, wherein said ultraviolet light energy comprises ultraviolet A light energy.

106. The computer system of claim 86, wherein said calculator configured to calculate said fluid's light energy value for delivery to said biological fluid includes:

a calculator configured to calculate an irradiation period required by a light energy source to deliver said fluid's light energy value.

107. The computer system of claim 106, wherein said calculator configured to calculate said fluid's light energy value for delivery to said biological fluid includes:

an obtainer to obtain a decay life value for said light energy source.

108. The computer system of claim 106, wherein said biological fluid comprises non-target material, wherein said non-target material comprises red blood cells, and wherein said calculator configured to calculate said fluid's light energy value for delivery to said biological fluid includes:

an obtainer to obtain a volume of biological fluid value;

an obtainer to obtain a percent of red blood cells value; and an obtainer to obtain a decay life value for said light energy source.

109. The computer system of claim 86, wherein said obtainer configured to obtain said target's effective light energy value includes:

an accessor configured to access a targets effective light energy value table.

110. The computer system of claim 86, wherein said obtainer configured to obtain an average light energy factor includes:

an accessor configured to access a light energy factor table.

111. The computer system of claim 110, wherein said obtainer configured to obtain said average light energy value at a unit surface area includes:

an accessor configured to access an average light energy value at a unit surface area table.

112. The computer system of claim 111, wherein said obtainer configured to obtain said light energy value at an incident surface includes:

an accessor configured to access a light energy value at an incident surface table.

113. The computer system of claim 112, wherein said non-target material comprises red blood cells.

114. The computer system of claim 86, wherein said obtainer configured to obtain an average light energy factor includes:

an obtainer configured to obtain an average light energy value at a unit surface area of the targets in the biological fluid;

an obtainer configured to obtain a light energy value at an incident surface of the biological fluid film; and a calculator configured to calculate the average light energy factor for said biological fluid.

115. The computer system of claim 114, wherein said biological fluid comprises leukocyte-rich buffy coat.

116. The computer system of claim 115, wherein said biological fluid is treated with a light energy activatable drug.

117. The computer system of claim 116, wherein said drug comprises 8-methoxypsoralen.

118. The computer system of claim 117, wherein said light energy comprises ultraviolet light energy.

119. The computer system of claim 118, wherein said ultraviolet light energy comprises ultraviolet A light energy.

120. The computer system of claim 86, wherein said obtainer configured to obtain an average light energy factor includes:

an obtainer configured to obtain a thickness ratio;

an obtainer configured to obtain a light transmittance value of a known fluid film thickness; and a calculator configured to calculate the average light energy factor for said biological fluid.

121. The computer system of claim 120, wherein said obtainer configured to obtain the thickness ratio further includes:

an accessor configured to access a thickness ratio table.

122. The computer system of claim 120, wherein said obtainer configured to obtain an irradiation period includes:

an accessor configured to access a irradiation period table.

123. The computer system of claim 120, wherein said non-target material comprises red blood cells.

124. The computer system of claim 120, wherein said biological fluid comprises leukocyte-rich buffy coat.

125. The computer system of claim 124, wherein said biological fluid is treated with a light energy activatable drug.

126. The computer system of claim 125, wherein said drug comprises 8-methoxypsoralen.

127. The computer system of claim 126, wherein said light energy comprises ultraviolet light energy.

128. The computer system of claim 127, wherein said ultraviolet light energy comprises ultraviolet A light energy.

129. The computer system of claim 120, wherein said obtainer configured to obtain the thickness ratio includes:

an obtainer configured to obtain a uniform thickness for said biological fluid;

an obtainer configured to obtain a thickness for said non-target; and a calculator configured to calculate the thickness ratio.

130. The computer system of claim 129, wherein said obtainer configured to obtain uniform film thickness includes:

an accessor configured to access a uniform thickness table.

131. The computer system of claim 129, wherein said obtainer configured to obtain said non-target thickness includes:

an accessor configured to access a non-target thickness table.

132. The computer system of claim 129, wherein said non-targets comprise red blood cells.

133. The computer system of claim 87, wherein said obtainer configured to obtain the average light energy factor includes:

an obtainer configured to obtain a thickness ratio;

an obtainer configured to obtain a red blood cell percentage for said biological fluid; and a calculator configured to calculate the average light energy factor for said targets in said biological fluid.

134. The computer system of claim 133, wherein said obtainer configured to obtain the thickness ratio includes:

an accessor configured to access a thickness ratio table.

135. The computer system of claim 133, wherein the obtainer configured to obtain the red blood cell percentage includes:

an accessor configured to access a red blood cell percentage table.

136. The computer system of claim 133, wherein said biological fluid comprises leukocyte-rich buffy coat.

137. The computer system of claim 136, wherein said biological fluid is treated with a light energy activatable drug.

138. The computer system of claim 137, wherein said drug comprises 8-methoxypsoralen.

139. The computer system of claim 138, wherein said light energy comprises ultraviolet light energy.

140. The computer system of claim 139, wherein said ultraviolet light energy comprises ultraviolet A light energy.

141. The computer system of claim 133, wherein said obtainer configured to obtain the thickness ratio includes:

an obtainer configured to obtain a uniform thickness for said biological fluid;

an obtainer configured to obtain a thickness for said non-target; and a calculator configured to calculate the thickness ratio.

142. The computer system of claim 141, wherein said obtainer configured to obtain the uniform film thickness includes:

an accessor configured to access an uniform thickness ratio table.

143. The computer system of claim 141, wherein said obtainer configured to obtain the thickness for said non-target comprises the step of:

an accessor configured to access a non-target thickness table.

144. A system for determining a fluid light energy value for delivery to a biological fluid comprising targets and non-target material, wherein an effective amount of light energy is desired to be delivered to said targets and wherein said non-target material attenuates said light energy passing through said biological fluid, comprising:

means for obtaining said target's effective light energy value;

means for obtaining an average light energy factor for said biological fluid; and means for calculating said fluid light energy value for delivery to said biological fluid, wherein determining the fluid light energy value is performed by one or more computer processors.

145. The system of claim 144, wherein obtaining said targets' effective light energy value comprises:

means for placing said targets in fluid, wherein said targets in said fluid do not receive attenuated light energy; and means for irradiating said fluid with sample light energy values.

146. The system of claim 144, wherein the obtaining said average light energy factor comprises:

means for obtaining the average light energy value at a unit surface area of the targets in the biological fluid;

means for obtaining the light energy value at an incident surface of the biological fluid film; and means for calculating the average light energy factor for said targets in said biological fluid.

147. The system of claim 144, wherein obtaining said average light energy factor comprises:

means for obtaining a thickness ratio;

means for obtaining a light transmittance value of a known fluid film thickness; and means for calculating the average light energy factor for said targets in said biological fluid.

148. The system of claim 147, wherein obtaining said thickness ratio comprises:

means for obtaining a uniform thickness for said biological fluid;

means for obtaining a thickness for said non-target; and means for calculating the thickness ratio.

149. The system of claim 144, wherein said non-target material comprises red blood cells and wherein obtaining the average light energy factor comprises:

means for obtaining a thickness ratio;

means for obtaining a red blood cell percentage for said biological fluid; and means for calculating the average light energy factor for said targets in said biological fluid.

150. The system of claim 149, wherein obtaining said thickness ratio comprises:

means for obtaining a uniform thickness for said biological fluid;

means for obtaining a thickness for said non-target; and means for calculating the thickness ratio.

151. The system of claim 144, wherein said non-target material comprises red blood cells and wherein obtaining the average light energy factor comprises:

means for obtaining a uniform thickness for said biological fluid;

means for obtaining a red blood cell percentage for said biological fluid; and means for calculating the average light energy factor for said targets in said biological fluid.

152. A computer readable medium containing instructions for controlling a computer system to perform a method, wherein the computer system determines a fluid light energy value for delivery to a biological fluid comprising targets and non-target material, wherein an effective amount of light energy is desired to be delivered to said targets, and wherein said non-target material attenuates said light energy passing through said biological fluid comprising:

obtaining said target's effective light energy value;

obtaining an average light energy factor for said targets in said biological fluid; and calculating the fluid's light energy value for delivery to said biological fluid, wherein determining the fluid light energy value is performed by one or more computer processors.

153. The computer readable medium of claim 152, wherein obtaining said target's effective light energy value comprises:

placing said targets in fluid, wherein said targets in said fluid do not receive attenuated light energy; and irradiating said fluid with sample light energy values.

154. The computer readable medium of claim 152, wherein the obtaining said average light energy factor comprises:

obtaining an average light energy value at a unit surface area of the targets in the biological fluid;

obtaining a light energy value at an incident surface of the biological fluid film; and calculating the average light energy factor for the targets in the biological fluid.

155. The computer readable medium of claim 152, wherein obtaining said average light energy factor comprises:

obtaining a thickness ratio;

obtaining a light transmittance value of a known fluid film thickness; and calculating the average light energy factor for said targets in said biological fluid.

156. The computer readable medium of claim 155, wherein obtaining said thickness ratio comprises:

obtaining a uniform thickness for said biological fluid;

obtaining a thickness for said non-target; and calculating the thickness ratio.

157. The computer readable medium of claim 152, wherein said non-target material comprises red blood cells and wherein obtaining the average light energy factor comprises:

obtaining a thickness ratio;

obtaining a red blood cell percentage for said biological fluid; and calculating the average light energy factor for said targets in said biological fluid.

158. The computer readable medium of claim 157, wherein obtaining said thickness ratio comprises:

obtaining a uniform thickness for said biological fluid;

obtaining a thickness for said non-target; and calculating the thickness ratio.

159. The computer readable medium of claim 152, wherein said non-target material comprises red blood cells and wherein obtaining the average light energy factor comprises:

obtaining a uniform thickness for said biological fluid;

obtaining a red blood cell percentage for said biological fluid; and calculating the average light energy factor for said targets in said biological fluid.

* * * * *

UNITED STATES PATENT AND TRADEMARK OFFICE
CERTIFICATE OF CORRECTION

PATENT NO. : 6,219,584 B1
DATED : April 17, 2001
INVENTOR(S) : Kyu Ho Lee

Page 1 of 1

It is certified that error appears in the above-identified patent and that said Letters Patent is hereby corrected as shown below:

IN THE TITLE OF THE INVENTION: Change "DELIVERY" to -- DELIVER --.

Column 25, claim 35,
Line 1, change "when" to -- wherein --.

Column 26, claim 62,
Line 1, change "28" to -- 57 --.

Column 27, claim 75,
Line 1, change "42" to -- 69 --.

Column 29, claim 111,
Line 1, change "110" to -- 114 --.

Signed and Sealed this

Sixth Day of November, 2001

Attest:

*Nicholas P. Godici*

NICHOLAS P. GODICI
*Attesting Officer*   *Acting Director of the United States Patent and Trademark Office*